US009587229B2

(12) United States Patent
Truppo et al.

(10) Patent No.: US 9,587,229 B2

(45) Date of Patent: Mar. 7, 2017

(54) IMMOBILIZED TRANSAMINASES AND PROCESS FOR MAKING AND USING IMMOBILIZED TRANSAMINASE

(75) Inventors: Matthew D. Truppo, Bradley Beach, NJ (US); Jacob M. Janey, New York, NY (US); Gregory Hughes, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/117,410

(22) PCT Filed: Jun. 18, 2012

(86) PCT No.: PCT/US2012/042853

§ 371 (c)(1), (2), (4) Date: Nov. 13, 2013

(87) PCT Pub. No.: WO2012/177527

PCT Pub. Date: Dec. 27, 2012

(65) Prior Publication Data

US 2014/0106413 A1 Apr. 17, 2014

Related U.S. Application Data

(60) Provisional application No. 61/500,642, filed on Jun. 24, 2011.

(51) Int. Cl.

| | |
|---|---|
| ***C12N 9/10*** | (2006.01) |
| ***C12P 13/00*** | (2006.01) |
| ***C12P 17/18*** | (2006.01) |
| ***C12N 11/08*** | (2006.01) |

(52) U.S. Cl.

CPC ............ *C12N 9/1096* (2013.01); *C12N 11/08* (2013.01); *C12P 13/001* (2013.01); *C12P 17/182* (2013.01); *Y02P 20/52* (2015.11)

(58) Field of Classification Search

None

See application file for complete search history.

(56) References Cited

U.S. PATENT DOCUMENTS

| | | | |
|---|---|---|---|
| 7,326,708 | B2 | 2/2008 | Cypes et al. |
| 7,468,459 | B2 | 12/2008 | Xiao et al. |
| 8,293,507 | B2 | 10/2012 | Savile et al. |
| 2010/0285541 | A1 | 11/2010 | Saville et al. |
| 2011/0033391 | A1 | 2/2011 | Weiner |

FOREIGN PATENT DOCUMENTS

| | | | |
|---|---|---|---|
| WO | WO03068909 | A2 | 8/2003 |
| WO | WO2007133184 | A2 | 11/2007 |
| WO | WO2011005477 | A1 | 1/2011 |
| WO | WO 2011017551 | A1 * | 2/2011 |

OTHER PUBLICATIONS

Petkar et al., Immobilization of lipases for non-aqueous synthesis, J. Mol. Catal. B, 2006, 39, 83-90.*

Hernandez, K. et al., Lipase B from Candida antarctica immobilized on octadecyl Sepabeads: A very stable biocatalyst in the presence of hydrogen peroxide, Process Biochemistry, 2011, p. 873-878, vol. 46.

Knezevic-Jugovic, Z. D. et al., The Immobilization of Lipase on Sepabeads: Coupling, Characterization and Application in Geranyl Butyrate Synthesis in a Low Aqueous System, Chemical Industry & Chemical Engineering Quarterly, 2008, p. 245-249, vol. 14, No. 4.

Martin, A. R. et al., Characterization of free and immobilized (S)-aminotransferase for acetophenone production, Appl Microbiol Biotechnol, 2007, p. 843-851, vol. 76.

Savile, C. K. et al., Biocatalytic Asymmetric Synthesis of Chiral Amines from Ketones Applied to Sitagliptin Manufacture, Science, 2010, p. 305-, vol. 329.

Sun, J. et al., Immobilization of Candida antarctica lipase B by adsorption in organic medium, New Biotechnology, 2010, p. 53-, vol. 27, No. 1.

Truppo, M. D. et al., Efficient kinetic resolution of racemic amines using a transaminase in combination with an amino acid oxidase, Chem. Commun, 2009, p. 2127-2129, 0.

Truppo, M. D. Eta L., Efficient Production of Enantiomerically Pure Chiral Amines at Concentrations of 50 g/L Using Transaminases, Organic Process Research & Development, 2010, p. 234-237, vol. 14.

Turner, N. J. et al., Chiral Amine Synthesis: Methods, Developments and Applications, Biocatalytic Routes to Nonracemic Chiral Amines, 2010, p. 441-455, 0.

Brena, B. M. et al, Immobilization of Enzymes, Methods in Biotechnology: Immobilization of Enzymes and Cells, 2006, p. 15-30.

Devine, H. G. et al., Arthrobacter sp. KNK168 variant transaminase SEQ:110, Database Geneseq, 2011, p. 1-2.

Hilterhaus, L. et al, Practical application of different enzymes immobilized on sepabeads, Bioprocess Biosyst Eng, 2008, p. 163-171, vol. 31.

Truppo, M. D. et al, Development of an Immobilized Transaminase Capable of Operating in Organic Solvent, ChemCatChem, 2012, p. 1071-1074, vol. 4, No. 8.

Song-Se Yi, et al, Covalent immobilization of w-transaminase from Vibrio fluvialis JS17 on chitosan beads, Process Biochemistry, 2007, p. 895-898, 42.

Brady, D. et al., Advances in enzyme immobilisation, Biotechnol Lett, 2009, p. 1639-1650, vol. 31.

Kunamneni, A. et al., Decolorization of synthetic dyes by laccase immobilized on epoxy-activated carriers, Process Biochemistry, 2008, p. 169-178, vol. 43.

Moreno, J. M. et al., Immobilization of alanine aminotransferase by covalent binding and entrapment, Biotechnol. Appl. Biochem, p. 231-235, vol. 23, 1996.

(Continued)

*Primary Examiner* — Robert Mondesi

*Assistant Examiner* — Todd M Epstein

(74) *Attorney, Agent, or Firm* — Janet E. Fair; Anna L. Cocuzzo

(57) ABSTRACT

The invention is directed to immobilized transaminases and methods of making and using them.

4 Claims, No Drawings

(56) References Cited

OTHER PUBLICATIONS

Palomo, J. M. et al., Interfacial adsorption of lipases on very hydrophobic support (octadecyl-Sepabeads): immobilization, hyperactivation and stabilization of the open form of lipases, Journal of Molecular Catalysis B: Enzymatic, 2002, p. 279-286, vol. 19-20.

Wehtje, E. et al., Improved Activity Retention of Enzymes Deposited on Solid Supports, Biotechnology and Bioengineering, 1993, p. 171-178, vol. 41.

Breuer, M. et al., Industrial Methods for the Production of Optically Active Intermediates, Angew. Chem. Int. Ed, 2004, p. 788-824, vol. 43.

* cited by examiner

SEQUENCE LISTING

```
<160> NUMBER OF SEQ ID NOS: 168

<210> SEQ ID NO 1
<211> LENGTH: 993
<212> TYPE: DNA
<213> ORGANISM: Artificial Sequence
<220> FEATURE:
<223> OTHER INFORMATION: ATA117

<400> SEQUENCE: 1

atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgttaccta caccgttttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcattcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggttctg gtttcaacgt tgttgttatc aaagacggtg ttgttcgttc tccgggtcgt     720
```

```
gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgcactaccg ctggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac taa                                 993


<210> SEQ ID NO 2
<211> LENGTH: 330
<212> TYPE: PRT
<213> ORGANISM: Artificial Sequence
<220> FEATURE:
<223> OTHER INFORMATION: ATA117

<400> SEQUENCE: 2

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Ser Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
```

```
305                 310                 315                 320

Ser Ser Ser Leu Leu Thr Pro Val Gln Tyr
                325                 330
```

```
<210> SEQ ID NO 3
<211> LENGTH: 990
<212> TYPE: DNA
<213> ORGANISM: Artificial Sequence
<220> FEATURE:
<223> OTHER INFORMATION: Variant of ATA117

<400> SEQUENCE: 3

atggctttct ctgctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgcactctg acgttaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcagtcgttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcagttcag    600

gaaacccacg accgtggttt cgaagctccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgcactaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 4
<211> LENGTH: 330
<212> TYPE: PRT
<213> ORGANISM: Artificial Sequence
<220> FEATURE:
<223> OTHER INFORMATION: Variant of ATA117

<400> SEQUENCE: 4

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110
```

```
Val Ala Lys Thr Glu Leu Arg Glu Ala Val Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 5
<211> LENGTH: 990
<212> TYPE: DNA
<213> ORGANISM: Artificial Sequence
<220> FEATURE:
<223> OTHER INFORMATION: Variant of ATA117

<400> SEQUENCE: 5

```
atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780
```

```
gaagctatcc tggctgacat caccctggct gaactgctgg acgctgacga agttctgggt    840

tgcactaccg ctggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 6
<211> LENGTH: 330
<212> TYPE: PRT
<213> ORGANISM: Artificial Sequence
<220> FEATURE:
<223> OTHER INFORMATION: Variant of ATA117

<400> SEQUENCE: 6

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
```

325 330

<210> SEQ ID NO 7
<211> LENGTH: 990
<212> TYPE: DNA
<213> ORGANISM: Artificial Sequence
<220> FEATURE:
<223> OTHER INFORMATION: Variant of ATA117

<400> SEQUENCE: 7

```
atggctttct ctgctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgcactctg acgttaccta caccgttttc cacgtttgga acggtaacgc tttccgtctg    240

gacgaccaca tcgaacgtct gttctctaac gctgaatcta tgcgtatcat cccgccgctg    300

acccaagacg aagttaaaga aatcgctctg gaactggttg ctaaaaccga gctgcgtgaa    360

gcattagttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcagttcag    600

gaaacccacg accgtggttt cgaagctccg ctgctgctgg acggtgacgg tctgctggct    660

gaaggtccgg gtttcaacgt tgttgttatc aaagacggtg ttgttcgttc tccgggtcgt    720

gctgctctgc cgggcatcac ccgtaaaacc gttctggaaa tcgctgaatc tctgggtcac    780

gaagctatcc tggctgacat caccctggct gaactgctgg acgctgacga agttctgggt    840

tgcactaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 8
<211> LENGTH: 330
<212> TYPE: PRT
<213> ORGANISM: Artificial Sequence
<220> FEATURE:
<223> OTHER INFORMATION: Variant of ATA117

<400> SEQUENCE: 8

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Leu Val Ser Val Ser Ile Thr
        115                 120                 125
```

```
Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 9
<211> LENGTH: 990
<212> TYPE: DNA
<213> ORGANISM: Artificial Sequence
<220> FEATURE:
<223> OTHER INFORMATION: Variant of ATA117

<400> SEQUENCE: 9

atggctttct ctgctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgcactctg acgttaccta caccgttttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaagctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgcactaccg gtggtggtgt ttggccgttc gtttctgttg acggtaaccc gatctctgac     900
```

```
ggtgttccgg gtccggttac ccagtctatc atccgtcgtt actgggaact gaacgttgaa    960

tcttcttctc tgctgacccc ggtacagtac                                     990


<210> SEQ ID NO 10
<211> LENGTH: 330
<212> TYPE: PRT
<213> ORGANISM: Artificial Sequence
<220> FEATURE:
<223> OTHER INFORMATION: Variant of ATA117

<400> SEQUENCE: 10

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 11
<211> LENGTH: 990
<212> TYPE: DNA
<213> ORGANISM: Artificial Sequence
<220> FEATURE:
<223> OTHER INFORMATION: Variant of ATA117

<400> SEQUENCE: 11

```
atggctttct ctgctgacac ctctgaaatc gtttacaccc acgacaccgg tctggactat     60
atcacctact ctgactacga actggacccg gctaacccgc tggctggtgg tgctgcttgg    120
atcgaaggtg ctttcgttcc gccgtctgaa gctcgtatct ctatcttcga ccagggttac    180
ctgcactctg acgttaccta caccgttttc cacgtttgga acggtaacgc tttccgtctg    240
gacgaccaca tcgaacgtct gttctctaac gctgaatcta tgcgtatcat cccgccgctg    300
acccaggacg aagttaaaga aatcgctctg gaactggttg ctaaaaccga actgcgtgaa    360
gcattagttt ctgtttctat cacccgtggt tactcttcta ccccaggtga acgtgacatc    420
accaaacatc gtccgcaggt ttacatgtac gctgttccgt accagtggat cgtaccgttt    480
gaccgcatcc gtgacggtgt tcacgctatg gttgctcagg ctgttcgtcg tactccgcgt    540
tcttctatcg acccgcaggt taaaaacttc cagtggggtg acctgatccg tgcagttcag    600
gaaacccacg accgtggttt cgaagctccg ctgctgctgg acggtgacgg tctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccctggct gaactgctgg acgctgacga agttctgggt    840
tgcactaccg gtggtggtgt ttggccgttc gtttctgttg acggtaaccc gatctctgac    900
ggtgttccgg gtccggttac ccagtctatc atccgtcgtt actgggaact gaacgttgaa    960
tcttcttctc tgctgacccc ggtacagtac                                     990
```

<210> SEQ ID NO 12
<211> LENGTH: 330
<212> TYPE: PRT
<213> ORGANISM: Artificial Sequence
<220> FEATURE:
<223> OTHER INFORMATION: Variant of ATA117

<400> SEQUENCE: 12

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Leu Val Ser Val Ser Ile Thr
        115                 120                 125

Arg Gly Tyr Ser Ser Thr Pro Gly Glu Arg Asp Ile Thr Lys His Arg
    130                 135                 140
```

```
Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ala Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 13
<211> LENGTH: 990
<212> TYPE: DNA
<213> ORGANISM: Artificial Sequence
<220> FEATURE:
<223> OTHER INFORMATION: Variant of ATA117

<400> SEQUENCE: 13

atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgcactctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccaggtga acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcagttcag     600

gaaacccacg accgtggttt cgaggctccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgcactaccg gtggtggtgt ttggccgttc gtttctgttg acggtaaccc gatctctgac     900

ggtgttccgg gtccggttac ccagtctatc atccgtcgtt actgggaact gaacgttgaa     960
```

tcttcttctc tgctgacccc ggtacagtac 990

<210> SEQ ID NO 14
<211> LENGTH: 330
<212> TYPE: PRT
<213> ORGANISM: Artificial Sequence
<220> FEATURE:
<223> OTHER INFORMATION: Variant of ATA117

<400> SEQUENCE: 14

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu His Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 15
<211> LENGTH: 990
<212> TYPE: DNA

<213> ORGANISM: Artificial Sequence
<220> FEATURE:
<223> OTHER INFORMATION: Variant of ATA117

<400> SEQUENCE: 15

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacttctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccaggtga acgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg ttctccgcgt    540

tcttctatcg acccgcaggt taaaaacttc cagtggggtg acctgatccg tgcatggcag    600

gaaacccacg accgtggttt cgaggctccg ctgctgctgg acggtgacgg tctgctggct    660

gaaggtccgg gttacaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 16
<211> LENGTH: 330
<212> TYPE: PRT
<213> ORGANISM: Artificial Sequence
<220> FEATURE:
<223> OTHER INFORMATION: Variant of ATA117

<400> SEQUENCE: 16

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Gly Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160
```

```
Asp Arg Ile Arg Asp Gly Val His Ala Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Trp Gln Glu Thr His Asp Arg Gly Phe Glu
        195                 200                 205

Ala Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 17
<211> LENGTH: 990
<212> TYPE: DNA
<213> ORGANISM: Artificial Sequence
<220> FEATURE:
<223> OTHER INFORMATION: Variant of ATA117

<400> SEQUENCE: 17

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgttctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcgtagtttt ctgtttctat cacccgtggt tactcttcta ccccatatga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gttacaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 18
<211> LENGTH: 330
<212> TYPE: PRT
<213> ORGANISM: Artificial Sequence
<220> FEATURE:
<223> OTHER INFORMATION: Variant of ATA117

<400> SEQUENCE: 18

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Phe Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Tyr Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 19
<211> LENGTH: 990
<212> TYPE: DNA
<213> ORGANISM: Artificial Sequence
<220> FEATURE:
<223> OTHER INFORMATION: Variant of ATA117

<400> SEQUENCE: 19

```
atggctttct ctgctgacac ctctgaaatc gtttacaccc acgacaccgg tctggactat     60
atcacctact ctgaccacga actggacccg gctaacccgc tggctggtgg tgctgcttgg    120
atcgaaggtg ctttcgttcc gccgtctgaa gctcgtatct ctatcttcga ccagggttac    180
ctgacctctg acgctaccta caccgggttc cacgtttgga acggtaacgc tttccgtctg    240
gacgaccaca tcgaacgtct gttctctaac gctgaatcta tgcgtatcat cccgccgctg    300
acccaggacg aagttaaaga aatcgctctg gaactggttg ctaaaaccga actgcgtgaa    360
gcagtagttt ctgtttctat cacccgtggt tactcttcta ccccatatac tcgtgacatc    420
accaaacatc gtccgcaggt ttacatgtac gctgttccgt accagtggat cgtaccgttt    480
gaccgcatcc gtgacggtgt tcacgctatg gttgctcagt ctgttcgtcg tactccgcgt    540
tcttctatcg acccgcaggt taaaaacttc cagtggggtg acctgatccg tgcaattcag    600
gaaacccacg accgtggttt cgagctgccg ctgctgctgg acggtgacgg tctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccctggct gaactgctgg acgctgatga agttctgggt    840
tgctcaaccg gtggtggtgt ttggccgttc gtttctgttg acggtaaccc gatctctgac    900
ggtgttccgg gtccggttac ccagtctatc atccgtcgtt actgggaact gaacgttgaa    960
tcttcttctc tgctgacccc ggtacagtac                                    990
```

<210> SEQ ID NO 20
<211> LENGTH: 330
<212> TYPE: PRT
<213> ORGANISM: Artificial Sequence
<220> FEATURE:
<223> OTHER INFORMATION: Variant of ATA117

<400> SEQUENCE: 20

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175
```

```
Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 21
<211> LENGTH: 990
<212> TYPE: DNA
<213> ORGANISM: Artificial Sequence
<220> FEATURE:
<223> OTHER INFORMATION: Variant of ATA117

<400> SEQUENCE: 21

atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccatatat tcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 22
<211> LENGTH: 330
<212> TYPE: PRT
```

```
<213> ORGANISM: Artificial Sequence
<220> FEATURE:
<223> OTHER INFORMATION: Variant of ATA117

<400> SEQUENCE: 22

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 23
<211> LENGTH: 990
<212> TYPE: DNA
<213> ORGANISM: Artificial Sequence
<220> FEATURE:
<223> OTHER INFORMATION: Variant of ATA117

<400> SEQUENCE: 23
```

```
atggctttct ctgctgacac ctctgaaatc gtttacaccc acgacaccgg tctggactat    60
atcacctact ctgaccacga actggacccg gctaacccgc tggctggtgg tgctgcttgg   120
atcgaaggtg ctttcgttcc gccgtctgaa gctcgtatct ctatcttcga ccagggttac   180
ctgacctctg acgctaccta caccgggttc cacgtttgga acggtaacgc tttccgtctg   240
gacgaccaca tcgaacgtct gttctctaac gctgaatcta tgcgtatcat cccgccgctg   300
acccaggacg aagttaaaga aatcgctctg gaactggttg ctaaaaccga actgcgtgaa   360
gcaatcgttt ctgtttctat cacccgtggt tactcttcta ccccatatac tcgtgacatc   420
accaaacatc gtccgcaggt ttacatgtac gctgttccgt accagtggat cgtaccgttt   480
gaccgcatcc gtgacggtgt tcacgctatg gttgctcagt ctgttcgtcg tactccgcgt   540
tcttctatcg acccgcaggt taaaaacttc cagtggggtg acctgatccg tgcaattcag   600
gaaacccacg accgtggttt cgagctgccg ctgctgctgg acggtgacgg tctgctggct   660
gaaggtccgg gttacaacgt tgttgttatc aaagacggtg ttgttcgttc tccgggtcgt   720
gctgctctgc cgggtatcac ccgtaaaacc gttctggaaa tcgctgaatc tctgggtcac   780
gaagctatcc tggctgacat caccctggct gaactgctgg acgctgacga agttctgggt   840
tgctcaaccg gtggtggtgt ttggccgttc gtttctgttg acggtaaccc gatctctgac   900
ggtgttccgg gtccggttac ccagtctatc atccgtcgtt actgggaact gaacgttgaa   960
tcttcttctc tgctgacccc ggtacagtac                                    990
```

```
<210> SEQ ID NO 24
<211> LENGTH: 330
<212> TYPE: PRT
<213> ORGANISM: Artificial Sequence
<220> FEATURE:
<223> OTHER INFORMATION: Variant of ATA117

<400> SEQUENCE: 24

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190
```

```
Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Tyr Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 25
<211> LENGTH: 990
<212> TYPE: DNA
<213> ORGANISM: Artificial Sequence
<220> FEATURE:
<223> OTHER INFORMATION: Variant of ATA117

<400> SEQUENCE: 25

atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgcactctg acgctaccta caccgggttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcagtagttt ctgtttctat cacccgtggt tactcttcta ccccatatat tcgtgacatc     420

accaaacatc gtccgcaggt ttacatgtac gctgttccgt accagtggat cgtaccgttt     480

gaccgcatcc gtgacggtgt tcacgctatg gttgctcagg ccgttcgtcg tactccgcgt     540

tcttctatcg acccgcaggt taaaaacttc cagtggggtg acctgatccg tgcaattcag     600

gaaacccacg accgtggttt cgagctgccg ctgctgctgg acggtgacgg tctgctggct     660

gaaggtccgg gtttcaacgt tgttgttgtc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgcactaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 26
<211> LENGTH: 330
<212> TYPE: PRT
<213> ORGANISM: Artificial Sequence
<220> FEATURE:
<223> OTHER INFORMATION: Variant of ATA117
```

<400> SEQUENCE: 26

Met Ala Phe Ser Ala Asp Thr Ser Glu Ile Val Tyr Thr His Asp Thr
1 5 10 15

Gly Leu Asp Tyr Ile Thr Tyr Ser Asp His Glu Leu Asp Pro Ala Asn
20 25 30

Pro Leu Ala Gly Gly Ala Ala Trp Ile Glu Gly Ala Phe Val Pro Pro
35 40 45

Ser Glu Ala Arg Ile Ser Ile Phe Asp Gln Gly Tyr Leu His Ser Asp
50 55 60

Ala Thr Tyr Thr Gly Phe His Val Trp Asn Gly Asn Ala Phe Arg Leu
65 70 75 80

Asp Asp His Ile Glu Arg Leu Phe Ser Asn Ala Glu Ser Met Arg Ile
85 90 95

Ile Pro Pro Leu Thr Gln Asp Glu Val Lys Glu Ile Ala Leu Glu Leu
100 105 110

Val Ala Lys Thr Glu Leu Arg Glu Ala Val Val Ser Val Ser Ile Thr
115 120 125

Arg Gly Tyr Ser Ser Thr Pro Tyr Ile Arg Asp Ile Thr Lys His Arg
130 135 140

Pro Gln Val Tyr Met Tyr Ala Val Pro Tyr Gln Trp Ile Val Pro Phe
145 150 155 160

Asp Arg Ile Arg Asp Gly Val His Ala Met Val Ala Gln Ala Val Arg
165 170 175

Arg Thr Pro Arg Ser Ser Ile Asp Pro Gln Val Lys Asn Phe Gln Trp
180 185 190

Gly Asp Leu Ile Arg Ala Ile Gln Glu Thr His Asp Arg Gly Phe Glu
195 200 205

Leu Pro Leu Leu Leu Asp Gly Asp Gly Leu Leu Ala Glu Gly Pro Gly
210 215 220

Phe Asn Val Val Val Val Lys Asp Gly Val Val Arg Ser Pro Gly Arg
225 230 235 240

Ala Ala Leu Pro Gly Ile Thr Arg Lys Thr Val Leu Glu Ile Ala Glu
245 250 255

Ser Leu Gly His Glu Ala Ile Leu Ala Asp Ile Thr Leu Ala Glu Leu
260 265 270

Leu Asp Ala Asp Glu Val Leu Gly Cys Thr Thr Gly Gly Gly Val Trp
275 280 285

Pro Phe Val Ser Val Asp Gly Asn Pro Ile Ser Asp Gly Val Pro Gly
290 295 300

Pro Val Thr Gln Ser Ile Ile Arg Arg Tyr Trp Glu Leu Asn Val Glu
305 310 315 320

Ser Ser Ser Leu Leu Thr Pro Val Gln Tyr
325 330

<210> SEQ ID NO 27
<211> LENGTH: 990
<212> TYPE: DNA
<213> ORGANISM: Artificial Sequence
<220> FEATURE:
<223> OTHER INFORMATION: Variant of ATA117

<400> SEQUENCE: 27
atggctttct ctgctgacac ctctgaaatc gtttacaccc acgacaccgg tctggactat 60
atcacctact ctgaccacga actggacccg gctaacccgc tggctggtgg tgctgcttgg 120

```
atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcacatgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 28
<211> LENGTH: 330
<212> TYPE: PRT
<213> ORGANISM: Artificial Sequence
<220> FEATURE:
<223> OTHER INFORMATION: Variant of ATA117

<400> SEQUENCE: 28

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala His Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205
```

```
Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 29
<211> LENGTH: 990
<212> TYPE: DNA
<213> ORGANISM: Artificial Sequence
<220> FEATURE:
<223> OTHER INFORMATION: Variant of ATA117

<400> SEQUENCE: 29

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccacgttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 30
<211> LENGTH: 330
<212> TYPE: PRT
<213> ORGANISM: Artificial Sequence
<220> FEATURE:
<223> OTHER INFORMATION: Variant of ATA117

<400> SEQUENCE: 30

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 31
<211> LENGTH: 990
<212> TYPE: DNA
<213> ORGANISM: Artificial Sequence
<220> FEATURE:
<223> OTHER INFORMATION: Variant of ATA117

<400> SEQUENCE: 31

```
atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180
```

```
ctgacctctg acgctaccta cacctgtttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 32
<211> LENGTH: 330
<212> TYPE: PRT
<213> ORGANISM: Artificial Sequence
<220> FEATURE:
<223> OTHER INFORMATION: Variant of ATA117

<400> SEQUENCE: 32

```
Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220
```

```
Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 33
<211> LENGTH: 990
<212> TYPE: DNA
<213> ORGANISM: Artificial Sequence
<220> FEATURE:
<223> OTHER INFORMATION: Variant of ATA117

<400> SEQUENCE: 33

atggctttct ctgctgacac ctctgaaatc gtttacaccc acgacaccgg tctggactat      60

atcacctact ctgaccacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgctttc cacgtttgga acggtaacgc tttccgtctg     240

gacgaccaca tcgaacgtct gttctctaac gctgaatcta tgcgtatcat cccgccgctg     300

acccaggacg aagttaaaga aatcgctctg gaactggttg ctaaaaccga actgcgtgaa     360

gcaatcgttt ctgtttctat cacccgtggt tactcttcta ccccatatat tcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg acggtgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 34
<211> LENGTH: 330
<212> TYPE: PRT
<213> ORGANISM: Artificial Sequence
<220> FEATURE:
<223> OTHER INFORMATION: Variant of ATA117

<400> SEQUENCE: 34

Met Ala Phe Ser Ala Asp Thr Ser Glu Ile Val Tyr Thr His Asp Thr
1               5                   10                  15
```

```
Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Ala Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 35
<211> LENGTH: 990
<212> TYPE: DNA
<213> ORGANISM: Artificial Sequence
<220> FEATURE:
<223> OTHER INFORMATION: Variant of ATA117

<400> SEQUENCE: 35

```
atggctttct ctgctgacac ctctgaaatc gtttacaccc acgacaccgg tctggactat     60

atcacctact ctgaccacga actggacccg gctaaccgc tggctggtgg tgctgcttgg    120

atcgaaggtg ctttcgttcc gccgtctgaa gctcgtatct ctatcttcga ccagggttac    180

tatacctctg acgctaccta caccgggttc cacgtttgga acggtaacgc tttccgtctg    240

gacgaccaca tcgaacgtct gttctctaac gctgaatcta tgcgtatcat cccgccgctg    300
```

```
acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 36
<211> LENGTH: 330
<212> TYPE: PRT
<213> ORGANISM: Artificial Sequence
<220> FEATURE:
<223> OTHER INFORMATION: Variant of ATA117

<400> SEQUENCE: 36

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 37
<211> LENGTH: 990
<212> TYPE: DNA
<213> ORGANISM: Artificial Sequence
<220> FEATURE:
<223> OTHER INFORMATION: Variant of ATA117

<400> SEQUENCE: 37

atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgtattctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccatatat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 38
<211> LENGTH: 330
<212> TYPE: PRT
<213> ORGANISM: Artificial Sequence
<220> FEATURE:
<223> OTHER INFORMATION: Variant of ATA117

<400> SEQUENCE: 38

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30
```

```
Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Tyr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 39
<211> LENGTH: 990
<212> TYPE: DNA
<213> ORGANISM: Artificial Sequence
<220> FEATURE:
<223> OTHER INFORMATION: Variant of ATA117

<400> SEQUENCE: 39

atggctttct ctgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gctgaatcta tgcgtatcat cccgccgctg    300

acccaggacg aagttaaaga aatcgctctg gaactggttg ctaaaaccga actgcgtgaa    360
```

```
gcaatcgttt ctgtttctat cacccgtggt tactcttcta ccccatttat tcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg acggtgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ctggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                    990


<210> SEQ ID NO 40
<211> LENGTH: 330
<212> TYPE: PRT
<213> ORGANISM: Artificial Sequence
<220> FEATURE:
<223> OTHER INFORMATION: Variant of ATA117

<400> SEQUENCE: 40

Met Ala Phe Ser Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

```
Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 41
<211> LENGTH: 990
<212> TYPE: DNA
<213> ORGANISM: Artificial Sequence
<220> FEATURE:
<223> OTHER INFORMATION: Variant of ATA117

<400> SEQUENCE: 41

```
atggcattct atgctgacac ctctgaaatc gtttacaccc acgacaccgg tctggactat     60

atcacctact ctgaccacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta caccgggttc cacgtttgga acggtaacgc tttccgtctg    240

gacgaccaca tcgaacgtct gttctctaac gcggaatcta tccgtatcat cccgccgctg    300

acccaggacg aagttaaaga aatcgctctg gaactggttg ctaaaaccga actgcgtgaa    360

gcaatcgttt ctgtttctat cacccgtggt tactcttcta ccccgtatac gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgatgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 42
<211> LENGTH: 330
<212> TYPE: PRT
<213> ORGANISM: Artificial Sequence
<220> FEATURE:
<223> OTHER INFORMATION: Variant of ATA117

<400> SEQUENCE: 42

```
Met Ala Phe Tyr Ala Asp Thr Ser Glu Ile Val Tyr Thr His Asp Thr
1               5                   10                  15

Gly Leu Asp Tyr Ile Thr Tyr Ser Asp His Glu Leu Asp Pro Ala Asn
            20                  25                  30

Pro Leu Ala Gly Gly Ala Ala Trp Ile Glu Gly Ala Phe Val Pro Pro
        35                  40                  45
```

```
Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 43
<211> LENGTH: 990
<212> TYPE: DNA
<213> ORGANISM: Artificial Sequence
<220> FEATURE:
<223> OTHER INFORMATION: Variant of ATA117

<400> SEQUENCE: 43

atggcattct ctgctgacac ctctgaaatc gtttacaccc acgacaccgg tctggactat      60

atcacctatt cggactacga actggatccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gcggaatcta tccgtattat cccgccgctg     300

acccaggacg aagttaaaga aatcgctctg gaactggttg ctaaaaccga actgcgtgaa     360

gcaatcgttt ctgtttctat cacccgtggt tactcttcta ccccatatat tcgtgacatc     420

accaaacatc gtccgcaggt ttacatgtac gctgttccgt accagtggat cgtaccgttt     480
```

```
gaccgcatcc gtgacggtgt tcacgctatg gttgctcagt ctgttcgtcg tactccgcgt    540

tcttctatcg acccgcaggt taaaaacttc cagtggggtg acctaatccg tgcaattcag    600

gaaacccacg accgtggttt cgagctgccg ctgctgctgg actgcgatgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                    990
```

<210> SEQ ID NO 44
<211> LENGTH: 330
<212> TYPE: PRT
<213> ORGANISM: Artificial Sequence
<220> FEATURE:
<223> OTHER INFORMATION: Variant of ATA117

<400> SEQUENCE: 44

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Ile Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270
```

```
Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 45
<211> LENGTH: 990
<212> TYPE: DNA
<213> ORGANISM: Artificial Sequence
<220> FEATURE:
<223> OTHER INFORMATION: Variant of ATA117

<400> SEQUENCE: 45

atggctttct cagctgacac ctctgaaatc gtttacaccc acgacaccgg tctggactat      60

atcacctatt cggactacga actggatccg gctaacccgc tggctggtgg tgctgcttgg     120

atcgaaggtg ctttcgttcc gccgtctgaa gctcgtatct ctatcttcga ccagggttac     180

ctgacctctg acgctaccta caccgggttc cacgtttgga acggtaacgc tttccgtctg     240

gacgaccaca tcgaacgtct gttctctaac gcggaatcta tccgtattat cccgccgctg     300

acccaggacg aagttaaaga gatcgctctg gaactggttg ctaaaaccga actgcgtgaa     360

gcaatcgttt ctgtttctat cacccgtggt tactcttcta ccccgtatac gcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgatgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                       990


<210> SEQ ID NO 46
<211> LENGTH: 330
<212> TYPE: PRT
<213> ORGANISM: Artificial Sequence
<220> FEATURE:
<223> OTHER INFORMATION: Variant of ATA117

<400> SEQUENCE: 46

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60
```

```
Ala Thr Tyr Thr Gly Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 47
<211> LENGTH: 990
<212> TYPE: DNA
<213> ORGANISM: Artificial Sequence
<220> FEATURE:
<223> OTHER INFORMATION: Variant of ATA117

<400> SEQUENCE: 47

atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

ctgacctctg acgctaccta cacctgtttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccatatac gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540
```

```
tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

```
<210> SEQ ID NO 48
<211> LENGTH: 330
<212> TYPE: PRT
<213> ORGANISM: Artificial Sequence
<220> FEATURE:
<223> OTHER INFORMATION: Variant of ATA117

<400> SEQUENCE: 48

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285
```

```
Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 49
<211> LENGTH: 990
<212> TYPE: DNA
<213> ORGANISM: Artificial Sequence
<220> FEATURE:
<223> OTHER INFORMATION: Variant of ATA117

<400> SEQUENCE: 49

atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

ctgacctctg acgctaccta cacctgtttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcaatcgttt ctgtttctat cacccgtggt tactcttcta ccccatatac gcgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttccatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 50
<211> LENGTH: 330
<212> TYPE: PRT
<213> ORGANISM: Artificial Sequence
<220> FEATURE:
<223> OTHER INFORMATION: Variant of ATA117

<400> SEQUENCE: 50

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Leu Thr Ser Asp
    50                  55                  60

Ala Thr Tyr Thr Cys Phe His Val Trp Asn Gly Asn Ala Phe Arg Leu
65                  70                  75                  80
```

```
Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 51
<211> LENGTH: 990
<212> TYPE: DNA
<213> ORGANISM: Artificial Sequence
<220> FEATURE:
<223> OTHER INFORMATION: Variant of ATA117

<400> SEQUENCE: 51

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta cacctccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccattcac acgtgacatc    420

accaaacatc gtccgcaggt ttacatgtac gctattccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660
```

```
gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990
```

<210> SEQ ID NO 52
<211> LENGTH: 330
<212> TYPE: PRT
<213> ORGANISM: Artificial Sequence
<220> FEATURE:
<223> OTHER INFORMATION: Variant of ATA117

<400> SEQUENCE: 52

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Ser Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Ile Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300
```

```
Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 53
<211> LENGTH: 990
<212> TYPE: DNA
<213> ORGANISM: Artificial Sequence
<220> FEATURE:
<223> OTHER INFORMATION: Variant of ATA117

<400> SEQUENCE: 53

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta cacctgtttc cacgtttgga acggtaacgc tttccgtctg     240

gacgaccaca tcgaacgtct gttctctaac gcggaatcta tccgtatcat cccgccgctg     300

acccaggacg aagttaaaga gatcgctctg gaactggttg ctaaaaccga actgcgtgaa     360

gcagtggttt ctgtttctat cacccgtggt tactcttcta ccccattcac acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccctggct gaactgctgg acgctgacga agttctgggt     840

tgctcaaccg gtggtggtgt ttggccgttc gtttctgttg acggtaaccc gatctctgac     900

ggtgttccgg gtccggttac ccagtctatc atccgtcgtt actgggaact gaacgttgaa     960

tcttcttctc tgctgacccc ggtacagtac                                      990


<210> SEQ ID NO 54
<211> LENGTH: 330
<212> TYPE: PRT
<213> ORGANISM: Artificial Sequence
<220> FEATURE:
<223> OTHER INFORMATION: Variant of ATA117

<400> SEQUENCE: 54

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95
```

```
Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

```
<210> SEQ ID NO 55
<211> LENGTH: 990
<212> TYPE: DNA
<213> ORGANISM: Artificial Sequence
<220> FEATURE:
<223> OTHER INFORMATION: Variant of ATA117

<400> SEQUENCE: 55

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta caccaccttc cacgtttgga acggtaacgc tttccgtctg     240

gacgaccaca tcgaacgtct gttctctaac gcggaatcta tccgtatcat cccgccgctg     300

actcaggacg aagttaaaga gatcgctctg gaactggttg ctaaaaccga actgcgtgaa     360

gcagtggttt ctgtttctat cacccgtggt tactcttcta ccccattcac acgtgacatc     420

accaaacatc gtccgcaggt ttacatgtac gctgttccgt accagtggat cgtaccgttt     480

gaccgcatcc gtgacggtgt tcacgctatg gttgctcagt ctgttcgtcg tactccgcgt     540

tcttctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720
```

```
gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 56
<211> LENGTH: 330
<212> TYPE: PRT
<213> ORGANISM: Artificial Sequence
<220> FEATURE:
<223> OTHER INFORMATION: Variant of ATA117

<400> SEQUENCE: 56

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Val Val Ser Val Ser Ile Thr
        115                 120                 125

Arg Gly Tyr Ser Ser Thr Pro Phe Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320
```

```
Ser Ser Ser Leu Leu Thr Pro Val Gln Tyr
                325                 330


<210> SEQ ID NO 57
<211> LENGTH: 990
<212> TYPE: DNA
<213> ORGANISM: Artificial Sequence
<220> FEATURE:
<223> OTHER INFORMATION: Variant of ATA117

<400> SEQUENCE: 57

atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 58
<211> LENGTH: 330
<212> TYPE: PRT
<213> ORGANISM: Artificial Sequence
<220> FEATURE:
<223> OTHER INFORMATION: Variant of ATA117

<400> SEQUENCE: 58

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110
```

```
Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 59
<211> LENGTH: 990
<212> TYPE: DNA
<213> ORGANISM: Artificial Sequence
<220> FEATURE:
<223> OTHER INFORMATION: Variant of ATA117

<400> SEQUENCE: 59

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcacatgttt ctgtttctat cacccgtggt tactcttcta ccccattcga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840
```

```
tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                     990


<210> SEQ ID NO 60
<211> LENGTH: 330
<212> TYPE: PRT
<213> ORGANISM: Artificial Sequence
<220> FEATURE:
<223> OTHER INFORMATION: Variant of ATA117

<400> SEQUENCE: 60

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala His Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 61
<211> LENGTH: 990
<212> TYPE: DNA
<213> ORGANISM: Artificial Sequence
<220> FEATURE:
<223> OTHER INFORMATION: Variant of ATA117

<400> SEQUENCE: 61

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacctctg acgctaccta cacctgtttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccatatac gcgtgacatc    420

accaaacatc gtccgcaggt ttacatgtac gctgttccgt accagtggat cgtaccgtta    480

gaccgcatcc gtgacggtgt tcacttaatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgctgg acgctgacga agttctgggt    840

tgctcaaccg gtggtggtgt ttggccgttc gtttctgttg acggtaaccc gatctctgac    900

ggtgttccgg gtccggtaac ccagtctatc atccgtcgtt actgggaact gaacgttgaa    960

tcttcttctc tgctgacccc ggtacagtac                                     990
```

<210> SEQ ID NO 62
<211> LENGTH: 330
<212> TYPE: PRT
<213> ORGANISM: Artificial Sequence
<220> FEATURE:
<223> OTHER INFORMATION: Variant of ATA117

<400> SEQUENCE: 62

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125
```

```
Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Leu
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 63
<211> LENGTH: 990
<212> TYPE: DNA
<213> ORGANISM: Artificial Sequence
<220> FEATURE:
<223> OTHER INFORMATION: Variant of ATA117

<400> SEQUENCE: 63

atggctttct cagctgacac ctctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacctctg acgctaccta cacctgtttc cacgtttgga acggtaacgc tttccgtctg     240

gacgaccaca tcgaacgtct gttctctaac gcggaatctc tgcgtatcat cccgccgctg     300

acccaggacg aagttaaaga gatcgctctg gaactggttg ctaaaaccga actgcgtgaa     360

gcaatcgttt ctgtttctat cacccgtggt tactcttcta ccccatatac gcgtgacatc     420

accaaacatc gtccgcaggt ttacatgtac gctgttccgt accagtggat cgtaccgttt     480

gaccgcatcc gtgacggtgt tcacttaatg gttgctcagt ctgttcgtcg tacgccgcgt     540

agctctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccttggct gaactgctgg acgctgacga agttctgggt     840

tgctcaaccg gtggtggtgt ttggccgttc gtttctgttg acggtaaccc gatctctgac     900
```

```
ggtgttccgg gtccgttaac ccagtctatc atccgtcgtt actgggaact gaacgttgaa     960

tcttcttctc tgctgacccc ggtacagtac                                      990


<210> SEQ ID NO 64
<211> LENGTH: 330
<212> TYPE: PRT
<213> ORGANISM: Artificial Sequence
<220> FEATURE:
<223> OTHER INFORMATION: Variant of ATA117

<400> SEQUENCE: 64

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Leu Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Tyr Thr Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Leu Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330


<210> SEQ ID NO 65
```

<211> LENGTH: 990
<212> TYPE: DNA
<213> ORGANISM: Artificial Sequence
<220> FEATURE:
<223> OTHER INFORMATION: Variant of ATA117

<400> SEQUENCE: 65

```
atggctttct cagctgacac ctctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta cacctgtttc cacgtttgga acggtaacgc tttccgtctg    240

gacgaccaca tcgaacgtct gttctctaac gcggaatcta tccgtatcat cccgccgctg    300

accctggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgttc gctattccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 66
<211> LENGTH: 330
<212> TYPE: PRT
<213> ORGANISM: Artificial Sequence
<220> FEATURE:
<223> OTHER INFORMATION: Variant of ATA117

<400> SEQUENCE: 66

```
Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Cys Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Leu Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140
```

```
Pro Gln Val Tyr Met Phe Ala Ile Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 67
<211> LENGTH: 990
<212> TYPE: DNA
<213> ORGANISM: Artificial Sequence
<220> FEATURE:
<223> OTHER INFORMATION: Variant of ATA117

<400> SEQUENCE: 67

```
atggcttctc cagctgacac cccggaaatc gtttacaccc acgacaccgg tctggactat     60

atcacctact ctgactacga actggacccg gctaacccgc tggctggtgg tgctgcttgg    120

atcgaaggtg ctttcgttcc ggcgtctgaa gctcgtatct ctatcttcga ccagggttac    180

tatacttctg acgctaccta caccaccttc cacgtttgga acggtaacgc tttccgtctg    240

ggggaccaca tcgaacgtct gttctctaac gcggaatcta ttcgtttgat cccgccgctg    300

accaaagacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcgtcc gtgacggtgt tcacgctatg gttgctcagt ctgttcgtcg tactccgcgt    540

agctctatcg acccgcaggt taaaaacttc cagtggggtg acctgatccg tgcaattcag    600

gaaacccacg accgtggttt cgagctgccg attctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gtttttgaaa tcgctgaatc tctgggtcac    780

gaagctatcc tggctgacat caccctggct gaactgtatg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 68
<211> LENGTH: 330
<212> TYPE: PRT
<213> ORGANISM: Artificial Sequence
<220> FEATURE:
<223> OTHER INFORMATION: Variant of ATA117

<400> SEQUENCE: 68

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Ala
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Lys Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Val Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Ile Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Phe Glu Ile Ala Glu
                245                 250                 255

Ser Leu Gly His Glu Ala Ile Leu Ala Asp Ile Thr Leu Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 69
<211> LENGTH: 990
<212> TYPE: DNA
<213> ORGANISM: Artificial Sequence
<220> FEATURE:
<223> OTHER INFORMATION: Variant of ATA117

<400> SEQUENCE: 69

```
atggctttct cagctgacac cccggaaatc gtttacaccc acgacaccgg tctggactat     60
atcacctact ctgactacga actggacccg gctaacccgc tggctggtgg tgctgcttgg    120
atcgaaggtg ctttcgttcc ggcgtctgaa gctcgtatct ctatcttcga ccagggttac    180
tatacttctg acgctaccta caccaccttc cacgtttgga acggtaacgc tttccgtctg    240
ggggaccaca tcgaacgtct gttctctaac gcggaatcta ttcgtattat cccgccgctg    300
acccaggacg aagttaaaga gatcgctctg gaactggttg ctaaaaccga actgcgtgaa    360
gcaatcgttt ctgtttctat cacccgtggt tactcttcta ccccattcga gcgtgacatc    420
accaaacatc gtccgcaggt ttacatgtat gctgttccgt accagtggat cgtaccgttt    480
gaccgcatcc gtgacggtgt tcacctgatg gttgctcagt ctgttcgtcg tactccgcgt    540
agctctatcg acccgcaggt taaaaacttc cagtggggtg acctgatccg tgcaattcag    600
gaaacccacg accgtggttt cgagctgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgctgg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

<210> SEQ ID NO 70
<211> LENGTH: 330
<212> TYPE: PRT
<213> ORGANISM: Artificial Sequence
<220> FEATURE:
<223> OTHER INFORMATION: Variant of ATA117

<400> SEQUENCE: 70

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Ala
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160
```

```
Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 71
<211> LENGTH: 990
<212> TYPE: DNA
<213> ORGANISM: Artificial Sequence
<220> FEATURE:
<223> OTHER INFORMATION: Variant of ATA117

<400> SEQUENCE: 71

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggttac    180

tatacttctg acgctaccta caccaccttc cacgtttgga acggtaacgc tttccgtctg    240

gacgaccaca tcgaacgtct gttctctaac gcggaatcta tccgtatcat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtac gctgttccgt accagtggat cgtaccgttt    480

gaccgcatcc gtgacggtgt tcacgctatg gttgctcagt ctgttcgtcg tactccgcgt    540

tcttctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccctggct gaactgctgg acgctgacga agttctgggt    840

tgctcaaccg gtggtggtgt ttggccgttc gtttctgttg acggtaaccc gatctctgac    900

ggtgttccgg gtccggttac ccagtctatc atccgtcgtt actgggaact gaacgttgaa    960

tcttcttctc tgctgacccc ggtacagtac                                      990
```

<210> SEQ ID NO 72

<211> LENGTH: 330
<212> TYPE: PRT
<213> ORGANISM: Artificial Sequence
<220> FEATURE:
<223> OTHER INFORMATION: Variant of ATA117

<400> SEQUENCE: 72

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Asp Asp His Ile Glu Arg Leu Phe Ser Asn Ala Glu Ser Ile Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Pro Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330
```

<210> SEQ ID NO 73
<211> LENGTH: 990
<212> TYPE: DNA
<213> ORGANISM: Artificial Sequence
<220> FEATURE:
<223> OTHER INFORMATION: Variant of ATA117

<400> SEQUENCE: 73

```
atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggttac     180

tatacttctg acgctaccta caccaccttc cacgtttgga acggtaacgc tttccgtctg     240

ggggaccaca tcgaacgtct gttctctaac gcggaatctt tgcgtttgat cccgccgctg     300

acccaggacg aagttaaaga gatcgctctg gaactggttg ctaaaaccga actgcgtgaa     360

gcaatcgttt ctgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacgctatg gttgctcagt ctgttcgtcg ttccccgcgt     540

agctctatcg acccgcaggt taaaaacttc cagtggggtg acctgatccg tgcaattcag     600

gaaacccacg accgtggttt cgagctgccg ctgctgctgg actgcgacgg tctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgctgg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990
```

<210> SEQ ID NO 74
<211> LENGTH: 330
<212> TYPE: PRT
<213> ORGANISM: Artificial Sequence
<220> FEATURE:
<223> OTHER INFORMATION: Variant of ATA117

<400> SEQUENCE: 74

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Tyr Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175
```

```
Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 75
<211> LENGTH: 990
<212> TYPE: DNA
<213> ORGANISM: Artificial Sequence
<220> FEATURE:
<223> OTHER INFORMATION: Variant of ATA117

<400> SEQUENCE: 75

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatcta ttcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctctgccgt accagtggat cgtaccgttt    480

gaccgcatcc gtgacggtgt tcacgctatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gtttttgaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                    990
```

<210> SEQ ID NO 76
<211> LENGTH: 330
<212> TYPE: PRT
<213> ORGANISM: Artificial Sequence
<220> FEATURE:
<223> OTHER INFORMATION: Variant of ATA117

<400> SEQUENCE: 76

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Leu Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Phe Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 77
<211> LENGTH: 990
<212> TYPE: DNA
<213> ORGANISM: Artificial Sequence
<220> FEATURE:
<223> OTHER INFORMATION: Variant of ATA117

<400> SEQUENCE: 77

```
atggctttct cagctgacac ccctgaaatc gtttacaccc acgacaccgg tctggactat     60
```

```
atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatctt tgcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgctgg acgctgacga agttctgggt    840

tgctcaaccg gtggtggtgt ttggccgttc gttactgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 78
<211> LENGTH: 330
<212> TYPE: PRT
<213> ORGANISM: Artificial Sequence
<220> FEATURE:
<223> OTHER INFORMATION: Variant of ATA117

<400> SEQUENCE: 78

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Ser Pro Arg Ser Ser Ile Asp Pro Gln Val Lys Asn Phe Gln Trp
            180                 185                 190
```

```
Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Leu Asp Ala Asp Glu Val Leu Gly Cys Ser Thr Gly Gly Gly Val Trp
        275                 280                 285

Pro Phe Val Thr Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 79
<211> LENGTH: 990
<212> TYPE: DNA
<213> ORGANISM: Artificial Sequence
<220> FEATURE:
<223> OTHER INFORMATION: Variant of ATA117

<400> SEQUENCE: 79

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 80
<211> LENGTH: 330
<212> TYPE: PRT
<213> ORGANISM: Artificial Sequence
<220> FEATURE:
<223> OTHER INFORMATION: Variant of ATA117

<400> SEQUENCE: 80

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 81
<211> LENGTH: 990
<212> TYPE: DNA
<213> ORGANISM: Artificial Sequence
<220> FEATURE:
<223> OTHER INFORMATION: Variant of ATA117

<400> SEQUENCE: 81

```
atggctttct cagctgacac ccctgaaatc gtttacaccc acgacaccgg tctggactat      60

atcacctact ctgactacga actggacccg gctaacccgc tggctggtgg tgctgcttgg     120
```

-continued

```
atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaac gcggaatctt tgcgtttgat cccgccgctg    300

acccaggacg aagttaaaga gatcgctctg gaactggttg ctaaaaccga actgcgtgaa    360

gcaatcgttt ctgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt ctgttcgtcg ttccccgcgt    540

agctctatcg acccgcaggt taaaaacttc cagtggggtg acctgatccg tgcaattcag    600

gaaacccacg accgtggttt cgagctgccg ctgctgctgg actgcgacgg tctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 82
<211> LENGTH: 330
<212> TYPE: PRT
<213> ORGANISM: Artificial Sequence
<220> FEATURE:
<223> OTHER INFORMATION: Variant of ATA117

<400> SEQUENCE: 82

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Leu Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Ser Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205
```

```
Leu Pro Leu Leu Leu Asp Cys Asp Gly Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 83
<211> LENGTH: 990
<212> TYPE: DNA
<213> ORGANISM: Artificial Sequence
<220> FEATURE:
<223> OTHER INFORMATION: Variant of ATA117

<400> SEQUENCE: 83

atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgtta ctgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 84
<211> LENGTH: 330
<212> TYPE: PRT
<213> ORGANISM: Artificial Sequence
<220> FEATURE:
<223> OTHER INFORMATION: Variant of ATA117

<400> SEQUENCE: 84

Met Ala Phe Ser Ala Asp Thr Pro Glu Ile Val Tyr Thr His Asp Thr
```

```
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 85
<211> LENGTH: 990
<212> TYPE: DNA
<213> ORGANISM: Artificial Sequence
<220> FEATURE:
<223> OTHER INFORMATION: Variant of ATA117

<400> SEQUENCE: 85

atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240
```

```
ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatcgttc atgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 86
<211> LENGTH: 330
<212> TYPE: PRT
<213> ORGANISM: Artificial Sequence
<220> FEATURE:
<223> OTHER INFORMATION: Variant of ATA117

<400> SEQUENCE: 86

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220
```

```
Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 87
<211> LENGTH: 990
<212> TYPE: DNA
<213> ORGANISM: Artificial Sequence
<220> FEATURE:
<223> OTHER INFORMATION: Variant of ATA117

<400> SEQUENCE: 87

atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgtta atgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagctgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 88
<211> LENGTH: 330
<212> TYPE: PRT
<213> ORGANISM: Artificial Sequence
<220> FEATURE:
<223> OTHER INFORMATION: Variant of ATA117

<400> SEQUENCE: 88

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
```

```
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 89
<211> LENGTH: 990
<212> TYPE: DNA
<213> ORGANISM: Artificial Sequence
<220> FEATURE:
<223> OTHER INFORMATION: Variant of ATA117

<400> SEQUENCE: 89

```
atggctttct cagctgacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300
```

```
acccaggacg aagttaaaga gatcgctctg gaactggttg ctaaaaccga actgcgtgaa    360

gcgatcgttt ctgtttctat cacccgtggt tactcttcta ccccattcga gcgtgacatc    420

accaaacatc gtccgcaggt ttacatgcat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990


<210> SEQ ID NO 90
<211> LENGTH: 330
<212> TYPE: PRT
<213> ORGANISM: Artificial Sequence
<220> FEATURE:
<223> OTHER INFORMATION: Variant of ATA117

<400> SEQUENCE: 90

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Ser Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met His Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 91
<211> LENGTH: 990
<212> TYPE: DNA
<213> ORGANISM: Artificial Sequence
<220> FEATURE:
<223> OTHER INFORMATION: Variant of ATA117

<400> SEQUENCE: 91

atggctttct cagctgacac ccctgaaatc gtttacaccc acgacaccgg tctggactat     60

ataacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggttc atgtttctat cacccgtggt tactcttcta ccccattcga gcgtgacatc    420

accaaacatc gtccgcaggt ttacatgcac gctagcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 92
<211> LENGTH: 330
<212> TYPE: PRT
<213> ORGANISM: Artificial Sequence
<220> FEATURE:
<223> OTHER INFORMATION: Variant of ATA117

<400> SEQUENCE: 92

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
```

```
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met His Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 93
<211> LENGTH: 990
<212> TYPE: DNA
<213> ORGANISM: Artificial Sequence
<220> FEATURE:
<223> OTHER INFORMATION: Variant of ATA117

<400> SEQUENCE: 93

```
atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgattgtta ccgtttctat cacccgtggt tactcttcta ccccattcga gcgtgacatc     420
```

```
accaaacatc gtccgcaggt ttacatgagt gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

```
<210> SEQ ID NO 94
<211> LENGTH: 330
<212> TYPE: PRT
<213> ORGANISM: Artificial Sequence
<220> FEATURE:
<223> OTHER INFORMATION: Variant of ATA117

<400> SEQUENCE: 94

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255
```

-continued

```
Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 95
<211> LENGTH: 990
<212> TYPE: DNA
<213> ORGANISM: Artificial Sequence
<220> FEATURE:
<223> OTHER INFORMATION: Variant of ATA117

<400> SEQUENCE: 95

atggctttct cagctgacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta acgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 96
<211> LENGTH: 330
<212> TYPE: PRT
<213> ORGANISM: Artificial Sequence
<220> FEATURE:
<223> OTHER INFORMATION: Variant of ATA117

<400> SEQUENCE: 96

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
```

```
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 97
<211> LENGTH: 990
<212> TYPE: DNA
<213> ORGANISM: Artificial Sequence
<220> FEATURE:
<223> OTHER INFORMATION: Variant of ATA117

<400> SEQUENCE: 97

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatcgttc atgtttctat cacccgtggt tactcttcta ccccattcga gcgtgacatc     420

accaaacatc gtccgcaggt ttacatgtat gctgttccgt accagtggat cgtaccgttt     480
```

```
gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagctgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 98
<211> LENGTH: 330
<212> TYPE: PRT
<213> ORGANISM: Artificial Sequence
<220> FEATURE:
<223> OTHER INFORMATION: Variant of ATA117

<400> SEQUENCE: 98

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val His Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270
```

```
Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 99
<211> LENGTH: 990
<212> TYPE: DNA
<213> ORGANISM: Artificial Sequence
<220> FEATURE:
<223> OTHER INFORMATION: Variant of ATA117

<400> SEQUENCE: 99

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta acgtttctat cacccgtggt tactcttcta ccccattcga gcgtgacatc    420

accaaacatc gtccgcaggt ttacatgtat gctgttccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 100
<211> LENGTH: 330
<212> TYPE: PRT
<213> ORGANISM: Artificial Sequence
<220> FEATURE:
<223> OTHER INFORMATION: Variant of ATA117

<400> SEQUENCE: 100

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
```

```
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 101
<211> LENGTH: 990
<212> TYPE: DNA
<213> ORGANISM: Artificial Sequence
<220> FEATURE:
<223> OTHER INFORMATION: Variant of ATA117

<400> SEQUENCE: 101

```
atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta acgtttctat cacccgtggt tactcttcta ccccattcga gcgtgacatc     420

accaaacatc gtccgcaggt ttacatgtat gctgttccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600
```

```
gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacactac                                     990
```

```
<210> SEQ ID NO 102
<211> LENGTH: 330
<212> TYPE: PRT
<213> ORGANISM: Artificial Sequence
<220> FEATURE:
<223> OTHER INFORMATION: Variant of ATA117

<400> SEQUENCE: 102

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Asn Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285
```

```
Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val His Tyr
                325                 330


<210> SEQ ID NO 103
<211> LENGTH: 990
<212> TYPE: DNA
<213> ORGANISM: Artificial Sequence
<220> FEATURE:
<223> OTHER INFORMATION: Variant of ATA117

<400> SEQUENCE: 103

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 104
<211> LENGTH: 330
<212> TYPE: PRT
<213> ORGANISM: Artificial Sequence
<220> FEATURE:
<223> OTHER INFORMATION: Variant of ATA117

<400> SEQUENCE: 104

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
```

```
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 105
<211> LENGTH: 990
<212> TYPE: DNA
<213> ORGANISM: Artificial Sequence
<220> FEATURE:
<223> OTHER INFORMATION: Variant of ATA117

<400> SEQUENCE: 105

```
atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgttacgat cacccgtggt tactcttcta ccccattcga gaaagacatc     420

accaaacatc gtccgcaagt ttacatgagc gctggcccgt acatgtggat cgtaccgttt     480

gaccgcatcc gtgacggtgt tcacctgatg gttgctcagt ctgttcgtcg tacaccgcgt     540

agctctatcg acccgcaggt taaaaacttc cagtggggtg acctgatccg tgcaattcaa     600

gaaacccacg accgtggttt cgagttgccg ctgctgctgg actgcgacaa cctgctggct     660
```

```
gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 106
<211> LENGTH: 330
<212> TYPE: PRT
<213> ORGANISM: Artificial Sequence
<220> FEATURE:
<223> OTHER INFORMATION: Variant of ATA117

<400> SEQUENCE: 106

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Lys Asp Ile Thr Lys His Arg
    130                 135                 140

Pro Gln Val Tyr Met Ser Ala Gly Pro Tyr Met Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300
```

```
Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 107
<211> LENGTH: 990
<212> TYPE: DNA
<213> ORGANISM: Artificial Sequence
<220> FEATURE:
<223> OTHER INFORMATION: Variant of ATA117

<400> SEQUENCE: 107

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttcgat cacccgtggt tactcttcta ccccattcga gcctgacatc     420

accaaacatc gtccgcgcgt ttacatgagc gcttccccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcaa     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 108
<211> LENGTH: 330
<212> TYPE: PRT
<213> ORGANISM: Artificial Sequence
<220> FEATURE:
<223> OTHER INFORMATION: Variant of ATA117

<400> SEQUENCE: 108

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
```

```
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Pro Asp Ile Thr Lys His Arg
    130                 135                 140

Pro Arg Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 109
<211> LENGTH: 990
<212> TYPE: DNA
<213> ORGANISM: Artificial Sequence
<220> FEATURE:
<223> OTHER INFORMATION: Variant of ATA117

<400> SEQUENCE: 109

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgttacgat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780
```

```
gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 110
<211> LENGTH: 330
<212> TYPE: PRT
<213> ORGANISM: Artificial Sequence
<220> FEATURE:
<223> OTHER INFORMATION: Variant of ATA117

<400> SEQUENCE: 110

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320
```

```
Pro Ser Ser Leu Leu Thr Pro Val Gln Tyr
                325                 330


<210> SEQ ID NO 111
<211> LENGTH: 990
<212> TYPE: DNA
<213> ORGANISM: Artificial Sequence
<220> FEATURE:
<223> OTHER INFORMATION: Variant of ATA117

<400> SEQUENCE: 111

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgccatc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990


<210> SEQ ID NO 112
<211> LENGTH: 330
<212> TYPE: PRT
<213> ORGANISM: Artificial Sequence
<220> FEATURE:
<223> OTHER INFORMATION: Variant of ATA117

<400> SEQUENCE: 112

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
```

```
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg His Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 113
<211> LENGTH: 990
<212> TYPE: DNA
<213> ORGANISM: Artificial Sequence
<220> FEATURE:
<223> OTHER INFORMATION: Variant of ATA117

<400> SEQUENCE: 113

```
atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt tgctatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840
```

```
tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990


<210> SEQ ID NO 114
<211> LENGTH: 330
<212> TYPE: PRT
<213> ORGANISM: Artificial Sequence
<220> FEATURE:
<223> OTHER INFORMATION: Variant of ATA117

<400> SEQUENCE: 114

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Ala Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 115
<211> LENGTH: 990
<212> TYPE: DNA
<213> ORGANISM: Artificial Sequence
<220> FEATURE:
<223> OTHER INFORMATION: Variant of ATA117

<400> SEQUENCE: 115

```
atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagcagat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990
```

<210> SEQ ID NO 116
<211> LENGTH: 330
<212> TYPE: PRT
<213> ORGANISM: Artificial Sequence
<220> FEATURE:
<223> OTHER INFORMATION: Variant of ATA117

<400> SEQUENCE: 116

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
```

```
    130                 135                 140

Pro Gln Val Tyr Met Ser Ala Cys Pro Tyr Gln Gln Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 117
<211> LENGTH: 990
<212> TYPE: DNA
<213> ORGANISM: Artificial Sequence
<220> FEATURE:
<223> OTHER INFORMATION: Variant of ATA117

<400> SEQUENCE: 117

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcg tggacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960
```

```
ccttcttctc tgctgacccc ggtacagtac                                  990


<210> SEQ ID NO 118
<211> LENGTH: 330
<212> TYPE: PRT
<213> ORGANISM: Artificial Sequence
<220> FEATURE:
<223> OTHER INFORMATION: Variant of ATA117

<400> SEQUENCE: 118

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Val Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 119
<211> LENGTH: 990
```

<212> TYPE: DNA
<213> ORGANISM: Artificial Sequence
<220> FEATURE:
<223> OTHER INFORMATION: Variant of ATA117

<400> SEQUENCE: 119

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttttatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 120
<211> LENGTH: 330
<212> TYPE: PRT
<213> ORGANISM: Artificial Sequence
<220> FEATURE:
<223> OTHER INFORMATION: Variant of ATA117

<400> SEQUENCE: 120

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Phe Met Ser Ala Cys Pro Tyr Gln Trp Ile Val Pro Phe
```

```
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 121
<211> LENGTH: 990
<212> TYPE: DNA
<213> ORGANISM: Artificial Sequence
<220> FEATURE:
<223> OTHER INFORMATION: Variant of ATA117

<400> SEQUENCE: 121

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgttat    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 122
<211> LENGTH: 330
<212> TYPE: PRT
<213> ORGANISM: Artificial Sequence
<220> FEATURE:
<223> OTHER INFORMATION: Variant of ATA117

<400> SEQUENCE: 122

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Tyr Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 123
<211> LENGTH: 990
<212> TYPE: DNA
<213> ORGANISM: Artificial Sequence
<220> FEATURE:

<223> OTHER INFORMATION: Variant of ATA117

<400> SEQUENCE: 123

```
atggcgttct cagcggacac ccctgaaatc gtttacaccc acgacaccgg tctggactat      60
atcacctact ctgactacga actggacccg gctaacccgc tggctggtgg tgctgcttgg     120
atcgaaggtg ctttcgttcc gccgtctgaa gctcgtatct ctatcttcga ccagggtttt     180
tatacttctg acgctaccta caccaccttc cacgtttgga acggtaacgc tttccgtctg     240
ggggaccaca tcgaacgtct gttctctaat gcggaatcta ttcgtttgat cccgccgctg     300
acccaggacg aagttaaaga gatcgctctg gaactggttg ctaaaaccga actgcgtgaa     360
gcgatggtta ccgtttctat cacccgtggt tactcttcta ccccattcga gcgtgacatc     420
accaaacatc gtccgcaggt ttacatgagc gcttgcccgt acgtgtggat cgtaccgttt     480
gaccgcatcc gtgacggtgt tcacctgatg gttgctcagt cagttcgtcg tacaccgcgt     540
agctctatcg acccgcaggt taaaaacttc cagtggggtg acctgatccg tgcaattcag     600
gaaacccacg accgtggttt cgagttgccg ctgctgctgg actgcgacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacat caccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                      990
```

<210> SEQ ID NO 124
<211> LENGTH: 330
<212> TYPE: PRT
<213> ORGANISM: Artificial Sequence
<220> FEATURE:
<223> OTHER INFORMATION: Variant of ATA117

<400> SEQUENCE: 124

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Val Trp Ile Val Pro Phe
145                 150                 155                 160

Asp Arg Ile Arg Asp Gly Val His Leu Met Val Ala Gln Ser Val Arg
```

```
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 125
<211> LENGTH: 990
<212> TYPE: DNA
<213> ORGANISM: Artificial Sequence
<220> FEATURE:
<223> OTHER INFORMATION: Variant of ATA117

<400> SEQUENCE: 125

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc ctgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 126
<211> LENGTH: 330
```

<212> TYPE: PRT
<213> ORGANISM: Artificial Sequence
<220> FEATURE:
<223> OTHER INFORMATION: Variant of ATA117

<400> SEQUENCE: 126

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Pro Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 127
<211> LENGTH: 990
<212> TYPE: DNA
<213> ORGANISM: Artificial Sequence
<220> FEATURE:
<223> OTHER INFORMATION: Variant of ATA117

<400> SEQUENCE: 127

```
atggcgttct cagcggacac ccctgaaatc gtttacaccc acgacaccgg tctggactat     60
atcacctact ctgactacga actggacccg gctaacccgc tggctggtgg tgctgcttgg    120
atcgaaggtg ctttcgttcc gccgtctgaa gctcgtatct ctatcttcga ccagggtttt    180
tatacttctg acgctaccta caccaccttc cacgtttgga acggtaacgc tttccgtctg    240
ggggaccaca tcgaacgtct gttctctaat gcggaatcta ttcgtttgat cccgccgctg    300
acccaggacg aagttaaaga gatcgctctg gaactggttg ctaaaaccga actgcgtgaa    360
gcgatggtta ccgtttctat cacccgtggt tactcttcta ccccattcga gcgtgacatc    420
accaaacatc gtccgcaggt ttacatgagc gcttgcccgt acacttggat cgtaccgttt    480
gaccgcatcc gtgacggtgt tcacctgatg gttgctcagt cagttcgtcg tacaccgcgt    540
agctctatcg acccgcaggt taaaaacttc cagtggggtg acctgatccg tgcaattcag    600
gaaacccacg accgtggttt cgagttgccg ctgctgctgg actgcgacaa cctgctggct    660
gaaggtccgg gtttcaacgt tgttgttatc aaagacggtg ttgttcgttc tccgggtcgt    720
gctgctctgc cgggtatcac ccgtaaaacc gttctggaaa tcgctgaatc tctgggtcac    780
gaagctatcc tggctgacat caccccggct gaactgtacg acgctgacga agttctgggt    840
tgctcaaccg gtggtggtgt ttggccgttc gtttctgttg acggtaactc tatctctgac    900
ggtgttccgg gtccggttac ccagtctatc atccgtcgtt actgggaact gaacgttgaa    960
ccttcttctc tgctgacccc ggtacagtac                                     990
```

```
<210> SEQ ID NO 128
<211> LENGTH: 330
<212> TYPE: PRT
<213> ORGANISM: Artificial Sequence
<220> FEATURE:
<223> OTHER INFORMATION: Variant of ATA117

<400> SEQUENCE: 128

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Thr Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
```

```
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 129
<211> LENGTH: 990
<212> TYPE: DNA
<213> ORGANISM: Artificial Sequence
<220> FEATURE:
<223> OTHER INFORMATION: Variant of ATA117

<400> SEQUENCE: 129

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctctg gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                     990
```

```
<210> SEQ ID NO 130
<211> LENGTH: 330
<212> TYPE: PRT
<213> ORGANISM: Artificial Sequence
<220> FEATURE:
```

<223> OTHER INFORMATION: Variant of ATA117

<400> SEQUENCE: 130

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Leu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 131
<211> LENGTH: 990
<212> TYPE: DNA
<213> ORGANISM: Artificial Sequence
<220> FEATURE:
<223> OTHER INFORMATION: Variant of ATA117

<400> SEQUENCE: 131

```
atggcgttct cagcggacac ccctgaaatc gtttacaccc acgacaccgg tattgactat     60
```

```
atcacctact ctgactacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 132
<211> LENGTH: 330
<212> TYPE: PRT
<213> ORGANISM: Artificial Sequence
<220> FEATURE:
<223> OTHER INFORMATION: Variant of ATA117

<400> SEQUENCE: 132

Met Ala Phe Ser Ala Asp Thr Pro Glu Ile Val Tyr Thr His Asp Thr
1               5                   10                  15

Gly Ile Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
```

```
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

```
<210> SEQ ID NO 133
<211> LENGTH: 990
<212> TYPE: DNA
<213> ORGANISM: Artificial Sequence
<220> FEATURE:
<223> OTHER INFORMATION: Variant of ATA117

<400> SEQUENCE: 133

atggcgttct cagcggacac ccctgaaatc gtttacaccc acgacaccgg tctggactat     60

atcacctact ctcagtacga actggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 134
<211> LENGTH: 330
<212> TYPE: PRT
<213> ORGANISM: Artificial Sequence
<220> FEATURE:
<223> OTHER INFORMATION: Variant of ATA117

<400> SEQUENCE: 134
```

```
Met Ala Phe Ser Ala Asp Thr Pro Glu Ile Val Tyr Thr His Asp Thr
1               5                   10                  15

Gly Leu Asp Tyr Ile Thr Tyr Ser Gln Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 135
<211> LENGTH: 990
<212> TYPE: DNA
<213> ORGANISM: Artificial Sequence
<220> FEATURE:
<223> OTHER INFORMATION: Variant of ATA117

<400> SEQUENCE: 135

```
atggcgttct cagcggacac ccctgaaatc gtttacaccc acgacaccgg tctggactat     60

atcacctact ctgactacga actggacccg gctaacccgc tggctggtgg tgctgcttgg    120

atcggtggtg ctttcgttcc gccgtctgaa gctcgtatct ctatcttcga ccagggtttt    180
```

```
tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 136
<211> LENGTH: 330
<212> TYPE: PRT
<213> ORGANISM: Artificial Sequence
<220> FEATURE:
<223> OTHER INFORMATION: Variant of ATA117

<400> SEQUENCE: 136

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Gly Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
```

```
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 137
<211> LENGTH: 990
<212> TYPE: DNA
<213> ORGANISM: Artificial Sequence
<220> FEATURE:
<223> OTHER INFORMATION: Variant of ATA117

<400> SEQUENCE: 137

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc ggattctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 138
<211> LENGTH: 330
<212> TYPE: PRT
<213> ORGANISM: Artificial Sequence
<220> FEATURE:
<223> OTHER INFORMATION: Variant of ATA117

<400> SEQUENCE: 138

Met Ala Phe Ser Ala Asp Thr Pro Glu Ile Val Tyr Thr His Asp Thr
1               5                   10                  15
```

```
Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Asp
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 139
<211> LENGTH: 990
<212> TYPE: DNA
<213> ORGANISM: Artificial Sequence
<220> FEATURE:
<223> OTHER INFORMATION: Variant of ATA117

<400> SEQUENCE: 139

atggcgttct cagcggacac ccctgaaatc gtttacaccc acgacaccgg tctggactat      60

atcacctact ctgactacga actggaccag gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240
```

```
ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 140
<211> LENGTH: 330
<212> TYPE: PRT
<213> ORGANISM: Artificial Sequence
<220> FEATURE:
<223> OTHER INFORMATION: Variant of ATA117

<400> SEQUENCE: 140

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Gln Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
```

```
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 141
<211> LENGTH: 990
<212> TYPE: DNA
<213> ORGANISM: Artificial Sequence
<220> FEATURE:
<223> OTHER INFORMATION: Variant of ATA117

<400> SEQUENCE: 141

atggcgttct cagcggacac ccctgaaatc gtttacaccc acgacaccgg tctggactat     60

atcacctact ctgactacga acctgacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 142
<211> LENGTH: 330
<212> TYPE: PRT
<213> ORGANISM: Artificial Sequence
<220> FEATURE:
<223> OTHER INFORMATION: Variant of ATA117

<400> SEQUENCE: 142

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Pro Asp Pro Ala Asn
            20                  25                  30
```

```
Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 143
<211> LENGTH: 990
<212> TYPE: DNA
<213> ORGANISM: Artificial Sequence
<220> FEATURE:
<223> OTHER INFORMATION: Variant of ATA117

<400> SEQUENCE: 143

```
atggcgttct cagcggacac ccctgaaatc gtttacaccc acgacaccgg tctggactat     60

atcacctact ctgactacga actggacccg gctaacccgc tggctggtgg tgctgcttgg    120

catgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360
```

```
gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

```
<210> SEQ ID NO 144
<211> LENGTH: 330
<212> TYPE: PRT
<213> ORGANISM: Artificial Sequence
<220> FEATURE:
<223> OTHER INFORMATION: Variant of ATA117

<400> SEQUENCE: 144

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp His Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
```

```
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 145
<211> LENGTH: 990
<212> TYPE: DNA
<213> ORGANISM: Artificial Sequence
<220> FEATURE:
<223> OTHER INFORMATION: Variant of ATA117

<400> SEQUENCE: 145

atggcgttct cagcggacac ccctgaaatc gtttacaccc acgacaccgg tctggactat      60

atcacctact ctgactacga actggacatg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 146
<211> LENGTH: 330
<212> TYPE: PRT
<213> ORGANISM: Artificial Sequence
<220> FEATURE:
<223> OTHER INFORMATION: Variant of ATA117

<400> SEQUENCE: 146

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Met Ala Asn
            20                  25                  30

Pro Leu Ala Gly Gly Ala Ala Trp Ile Glu Gly Ala Phe Val Pro Pro
        35                  40                  45
```

```
Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 147
<211> LENGTH: 990
<212> TYPE: DNA
<213> ORGANISM: Artificial Sequence
<220> FEATURE:
<223> OTHER INFORMATION: Variant of ATA117

<400> SEQUENCE: 147

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatcc atatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420
```

```
accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 148
<211> LENGTH: 330
<212> TYPE: PRT
<213> ORGANISM: Artificial Sequence
<220> FEATURE:
<223> OTHER INFORMATION: Variant of ATA117

<400> SEQUENCE: 148

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile His Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
```

```
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 149
<211> LENGTH: 990
<212> TYPE: DNA
<213> ORGANISM: Artificial Sequence
<220> FEATURE:
<223> OTHER INFORMATION: Variant of ATA117

<400> SEQUENCE: 149

atggcgttct cagcggacac ccctgaaatc gtttacaccc acgacaccgg ttgtgactat     60

atcacctact ctgactacga actggacccg gctaacccgc tggctggtgg tgctgcttgg    120

atcgaaggtg ctttcgttcc gccgtctgaa gctcgtatct ctgtcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 150
<211> LENGTH: 330
<212> TYPE: PRT
<213> ORGANISM: Artificial Sequence
<220> FEATURE:
<223> OTHER INFORMATION: Variant of ATA117

<400> SEQUENCE: 150

Met Ala Phe Ser Ala Asp Thr Pro Glu Ile Val Tyr Thr His Asp Thr
1               5                   10                  15

Gly Cys Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Val Phe Asp Gln Gly Phe Tyr Thr Ser Asp
    50                  55                  60
```

```
Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 151
<211> LENGTH: 990
<212> TYPE: DNA
<213> ORGANISM: Artificial Sequence
<220> FEATURE:
<223> OTHER INFORMATION: Variant of ATA117

<400> SEQUENCE: 151

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gggttctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540
```

```
agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

<210> SEQ ID NO 152
<211> LENGTH: 330
<212> TYPE: PRT
<213> ORGANISM: Artificial Sequence
<220> FEATURE:
<223> OTHER INFORMATION: Variant of ATA117

<400> SEQUENCE: 152

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Gly
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
```

```
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 153
<211> LENGTH: 990
<212> TYPE: DNA
<213> ORGANISM: Artificial Sequence
<220> FEATURE:
<223> OTHER INFORMATION: Variant of ATA117

<400> SEQUENCE: 153

atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc ggtttctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 154
<211> LENGTH: 330
<212> TYPE: PRT
<213> ORGANISM: Artificial Sequence
<220> FEATURE:
<223> OTHER INFORMATION: Variant of ATA117

<400> SEQUENCE: 154

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Val
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80
```

```
Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 155
<211> LENGTH: 990
<212> TYPE: DNA
<213> ORGANISM: Artificial Sequence
<220> FEATURE:
<223> OTHER INFORMATION: Variant of ATA117

<400> SEQUENCE: 155

```
atggcgttct cagcggacac ccctgaaatc gtttacaccc acgacaccgg tctggactat     60

atcacctact ctgactacga actggacccg gctaacccgc tggctggtgg tgctgcttgg    120

tctgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600
```

```
gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                      990
```

<210> SEQ ID NO 156
<211> LENGTH: 330
<212> TYPE: PRT
<213> ORGANISM: Artificial Sequence
<220> FEATURE:
<223> OTHER INFORMATION: Variant of ATA117

<400> SEQUENCE: 156

```
Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ser Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
```

```
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 157
<211> LENGTH: 990
<212> TYPE: DNA
<213> ORGANISM: Artificial Sequence
<220> FEATURE:
<223> OTHER INFORMATION: Variant of ATA117

<400> SEQUENCE: 157

atggcgttct cagcggacac ccctgaaatc gtttacaccc acgacaccgg tctggactat     60

atcacctact ctgactacac tctggacccg gctaacccgc tggctggtgg tgctgcttgg    120

atcgaaggtg ctttcgttcc gccgtctgaa gctcgtatct ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgtttctat cacccgtggt tactcttcta ccccattcga gcgtgacatc    420

accaaacatc gtccgcaggt ttacatgagc gcttgcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg accgtggttt cgagttgccg ctgctgctgg actgcgacaa cctgctggct    660

gaaggtccgg gtttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990


<210> SEQ ID NO 158
<211> LENGTH: 330
<212> TYPE: PRT
<213> ORGANISM: Artificial Sequence
<220> FEATURE:
<223> OTHER INFORMATION: Variant of ATA117

<400> SEQUENCE: 158

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Thr Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95
```

```
Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 159
<211> LENGTH: 990
<212> TYPE: DNA
<213> ORGANISM: Artificial Sequence
<220> FEATURE:
<223> OTHER INFORMATION: Variant of ATA117

<400> SEQUENCE: 159

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatcc ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720
```

```
gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 160
<211> LENGTH: 330
<212> TYPE: PRT
<213> ORGANISM: Artificial Sequence
<220> FEATURE:
<223> OTHER INFORMATION: Variant of ATA117

<400> SEQUENCE: 160

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Pro Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
```

```
305                 310                 315                 320

Pro Ser Ser Leu Leu Thr Pro Val Gln Tyr
                325                 330


<210> SEQ ID NO 161
<211> LENGTH: 990
<212> TYPE: DNA
<213> ORGANISM: Artificial Sequence
<220> FEATURE:
<223> OTHER INFORMATION: Variant of ATA117

<400> SEQUENCE: 161

atggcgttct cagcggacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gcagtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgtttctat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780

gaagctatcc tggctgacat caccccggct gaactgtacg acgctgacga agttctgggt     840

tgctcaaccg gtggtggtgt ttggccgttc gtttctgttg acggtaactc tatctctgac     900

ggtgttccgg gtccggttac ccagtctatc atccgtcgtt actgggaact gaacgttgaa     960

ccttcttctc tgctgacccc ggtacagtac                                      990


<210> SEQ ID NO 162
<211> LENGTH: 330
<212> TYPE: PRT
<213> ORGANISM: Artificial Sequence
<220> FEATURE:
<223> OTHER INFORMATION: Variant of ATA117

<400> SEQUENCE: 162

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Gln
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110
```

```
Val Ala Lys Thr Glu Leu Arg Glu Ala Met Val Thr Val Ser Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330


<210> SEQ ID NO 163
<211> LENGTH: 990
<212> TYPE: DNA
<213> ORGANISM: Artificial Sequence
<220> FEATURE:
<223> OTHER INFORMATION: Variant of ATA117

<400> SEQUENCE: 163

atggcgttct caaaagacac ccctgaaatc gtttacaccc acgacaccgg tctggactat      60

atcacctact ctgactacga actggacccg gctaacccgc tggctggtgg tgctgcttgg     120

atcgaaggtg ctttcgttcc gccgtctgaa gctcgtatct ctatcttcga ccagggtttt     180

tatacttctg acgctaccta caccaccttc cacgtttgga acggtaacgc tttccgtctg     240

ggggaccaca tcgaacgtct gttctctaat gcggaatcta ttcgtttgat cccgccgctg     300

acccaggacg aagttaaaga gatcgctctg gaactggttg ctaaaaccga actgcgtgaa     360

gcgatggtta ccgttacgat cacccgtggt tactcttcta ccccattcga gcgtgacatc     420

accaaacatc gtccgcaggt ttacatgagc gcttgcccgt accagtggat cgtaccgttt     480

gaccgcatcc gtgacggtgt tcacctgatg gttgctcagt cagttcgtcg tacaccgcgt     540

agctctatcg acccgcaggt taaaaacttc cagtggggtg acctgatccg tgcaattcag     600

gaaacccacg accgtggttt cgagttgccg ctgctgctgg actgcgacaa cctgctggct     660

gaaggtccgg gtttcaacgt tgttgttatc aaagacggtg ttgttcgttc tccgggtcgt     720

gctgctctgc cgggtatcac ccgtaaaacc gttctggaaa tcgctgaatc tctgggtcac     780
```

```
gaagctatcc tggctgacat caccccggct gaactgtacg acgctgacga agttctgggt    840

tgctcaaccg gtggtggtgt ttggccgttc gtttctgttg acggtaactc tatctctgac    900

ggtgttccgg gtccggttac ccagtctatc atccgtcgtt actgggaact gaacgttgaa    960

ccttcttctc tgctgacccc ggtacagtac                                     990
```

```
<210> SEQ ID NO 164
<211> LENGTH: 330
<212> TYPE: PRT
<213> ORGANISM: Artificial Sequence
<220> FEATURE:
<223> OTHER INFORMATION: Variant of ATA117

<400> SEQUENCE: 164

Met Ala Phe Ser Lys Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Cys Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
```

325 330

<210> SEQ ID NO 165
<211> LENGTH: 990
<212> TYPE: DNA
<213> ORGANISM: Artificial Sequence
<220> FEATURE:
<223> OTHER INFORMATION: Variant of ATA117

<400> SEQUENCE: 165
atggcgttct cagcggacac ccctgaaatc gtttacaccc acgacaccgg tctggactat 60
atcacctact ctgactacga actggacccg gctaacccgc tggctggtgg tgctgcttgg 120
atcgaaggtg ctttcgttcc gccgacggaa gctcgtatct ctatcttcga ccagggtttt 180
tatacttctg acgctaccta caccaccttc cacgtttgga acggtaacgc tttccgtctg 240
ggggaccaca tcgaacgtct gttctctaat gcggaatcta ttcgtttgat cccgccgctg 300
acccaggacg aagttaaaga gatcgctctg gaactggttg ctaaaaccgg cctgcgtgaa 360
gcgatggtta ccgttacgat cacccgtggt tactcttcta ccccattcga gcgtgacatc 420
accaaacatc gtccgcaggt ttacatgagc gctagcccgt accagtggat cgtaccgttt 480
gaccgcatcc gtgacggtgt tcacctgatg gttgctcagt cagttcgtcg tacaccgcgt 540
agctctatcg acccgcaggt taaaaacttc cagtggggtg acctgatccg tgcaattcag 600
gaaacccacg accgtggttt cgagttgccg ctgctgctgg actgcgacaa cctgctggct 660
gaaggtccgg gtttcaacgt tgttgttatc aaagacggtg ttgttcgttc tccgggtcgt 720
gctgctctgc cgggtatcac ccgtaaaacc gttctggaaa tcgctgaatc tctgggtcac 780
gaagctatcc tggctgacat caccccggct gaactgtacg acgctgacga agttctgggt 840
tgctcaaccg gtggtggtgt ttggccgttc gtttctgttg acggtaactc tatctctgac 900
ggtgccccgg gtccggttac ccagtctatc atccgtcgtt actgggaact gaacgttgaa 960
ccttcttctc tgctgacccc ggtacagtac 990

<210> SEQ ID NO 166
<211> LENGTH: 330
<212> TYPE: PRT
<213> ORGANISM: Artificial Sequence
<220> FEATURE:
<223> OTHER INFORMATION: Variant of ATA117

<400> SEQUENCE: 166

Met Ala Phe Ser Ala Asp Thr Pro Glu Ile Val Tyr Thr His Asp Thr
1 5 10 15

Gly Leu Asp Tyr Ile Thr Tyr Ser Asp Tyr Glu Leu Asp Pro Ala Asn
20 25 30

Pro Leu Ala Gly Gly Ala Ala Trp Ile Glu Gly Ala Phe Val Pro Pro
35 40 45

Thr Glu Ala Arg Ile Ser Ile Phe Asp Gln Gly Phe Tyr Thr Ser Asp
50 55 60

Ala Thr Tyr Thr Thr Phe His Val Trp Asn Gly Asn Ala Phe Arg Leu
65 70 75 80

Gly Asp His Ile Glu Arg Leu Phe Ser Asn Ala Glu Ser Ile Arg Leu
85 90 95

Ile Pro Pro Leu Thr Gln Asp Glu Val Lys Glu Ile Ala Leu Glu Leu
100 105 110

Val Ala Lys Thr Gly Leu Arg Glu Ala Met Val Thr Val Thr Ile Thr
115 120 125

```
Arg Gly Tyr Ser Ser Thr Pro Phe Glu Arg Asp Ile Thr Lys His Arg
    130                 135                 140

Pro Gln Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Ala Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

<210> SEQ ID NO 167
<211> LENGTH: 990
<212> TYPE: DNA
<213> ORGANISM: Artificial Sequence
<220> FEATURE:
<223> OTHER INFORMATION: Variant of ATA117

<400> SEQUENCE: 167

```
atggcgttct cagcggacac ccctgaaatc gtttacaccc acgacaccgg tctggactat     60

atcacctact ctgactacga actggacccg gctaacccgc tggctggtgg tgctgcttgg    120

atcgaaggtg ctttcgttcc gccgtctgaa gctcgtatcc ctatcttcga ccagggtttt    180

tatacttctg acgctaccta caccaccttc cacgtttgga acggtaacgc tttccgtctg    240

ggggaccaca tcgaacgtct gttctctaat gcggaatcta ttcgtttgat cccgccgctg    300

acccaggacg aagttaaaga gatcgctctg gaactggttg ctaaaaccga actgcgtgaa    360

gcgatggtta ccgttacgat cacccgtggt tactcttcta ccccattcga gcgtgacatc    420

accaaacatc gtccgcaggt ttacatgagc gctagcccgt accagtggat cgtaccgttt    480

gaccgcatcc gtgacggtgt tcacctgatg gttgctcagt cagttcgtcg tacaccgcgt    540

agctctatcg acccgcaggt taaaaacttc cagtggggtg acctgatccg tgcaattcag    600

gaaacccacg ctcgtggttt cgagttgccg ctgctgctgg actgcgacaa cctgctggct    660

gaaggtccgg gcttcaacgt tgttgttatc aaagacggtg ttgttcgttc tccgggtcgt    720

gctgctctgc cgggtatcac ccgtaaaacc gttctggaaa tcgctgaatc tctgggtcac    780

gaagctatcc tggctgacat caccccggct gaactgtacg acgctgacga agttctgggt    840

tgctcaaccg gtggtggtgt ttggccgttc gtttctgttg acggtaactc tatctctgac    900
```

```
ggtgttccgg gtccggttac ccagtctatc atccgtcgtt actgggaact gaacgttgaa    960

ccttcttctc tgctgacccc ggtacagtac                                     990


<210> SEQ ID NO 168
<211> LENGTH: 330
<212> TYPE: PRT
<213> ORGANISM: Artificial Sequence
<220> FEATURE:
<223> OTHER INFORMATION: Variant of ATA117

<400> SEQUENCE: 168

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Pro Ile Phe Asp Gln Gly Phe Tyr Thr Ser Asp
    50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
    130                 135                 140

Pro Gln Val Tyr Met Ser Ala Ser Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Ala Arg Gly Phe Glu
        195                 200                 205

Leu Pro Leu Leu Leu Asp Cys Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330
```

IMMOBILIZED TRANSAMINASES AND PROCESS FOR MAKING AND USING IMMOBILIZED TRANSAMINASE

TECHNICAL FIELD OF THE INVENTION

The invention is directed to immobilized transaminases and methods of making and using them.

BACKGROUND OF THE INVENTION

Enzymes are protein molecules which serve to accelerate the chemical reactions of living cells (often by several orders of magnitude). Without enzymes, most biochemical reactions would be too slow to even carry out life processes. Enzymes display great specificity and are not permanently modified by their participation in reactions. Since they are not changed during the reactions, enzymes can be cost effectively used as catalysts for a desired chemical transformation.

Transaminases are a specific class of enzymes that catalyze the direct amination of ketones to chiral amines. Enantiomerically pure chiral amines are key intermediates in a number of pharmaceutical compounds that possess a wide range of biological activities. Currently there is considerable effort underway to develop efficient catalytic methods for their preparation utilizing biocatalysts. Recently transaminases have emerged as promising biocatalysts for chiral amine production. Truppo et al., *Efficient kinetic resolution of recemic amines using a transaminase in combination with an amino acid oxidase*, Chem. Commun., 2009, 2127-2129; and Truppo et al., *Efficient Production of Enantiomerically Pure Chiral Amines at Concentrations of* 50 g/L *Using Transaminases*, Organic Process Research & Development 2010, 14, 234-237.

For example, rhodium-catalized asymmetric enamine hydrogenation was originally used for the large-scale manufacture of the antidiabetic compound sitagliptin. The rhodium was replaced with a transaminase which ultimately has lead to an enzymatic process that reduces waste, improves yield and safety, and eliminates the need for a metal catalyst. Moreover, the resultant biocatalyst showed broad applicability toward the synthesis of chiral amines that previously were accessible only via resolution. Savile et al., *Biocatalytic Asymmetric Synthesis of Chiral Amines from Ketones Applied to Sitagliptin Manufacture*, Science, Vol. 329, pgs. 305-309, 16 Jul. 2010.

Though advances in producing chiral amines using transaminases have been highly regarded, there still exits some drawbacks to the enzymatic process. Currently enzymatic processes can only be run in aqueous solvent systems as the transaminases are not stable in 100% organic solvents. Additionally, during product amine isolation, the transaminase catalyst is deactivated and discarded resulting in the inability to reuse the catalyst.

Thus, though attempts have been made to immobilize transaminases none have been successful in overcoming their lack of stability, more specifically their lack of stability in organic solvents.

SUMMARY OF THE INVENTION

Described herein, are immobilized transaminases comprising a recombinant transaminase physically attached to a resin by ether hydrophobic interactions or covalent bonds. The immobilized transaminases described herein include recombinant transaminases that are capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels measurable by an analysis technique. In certain embodiments the immobilized transaminases described herein are used to make (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

In certain embodiments, described herein are immobilized transaminases comprising a recombinant transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-c]pyrazin-7(8H)-yl]-1-(2,4,5-trifluorophenyl)butan-2-amine in the presence of an amino group donor to levels measurable by an analysis technique; and a resin, wherein the recombinant transaminase is attached to the resin by covalent bonds or hydrophobic interactions, and wherein the immobilized transaminase is stable in a solvent system that comprises at least 90% of organic solvents.

For example in one embodiment, the recombinant transaminase is attached to a resin by hydrophobic interactions. In another embodiment, the recombinant transaminase is attached to a resin by covalent bonds.

The immobilized transaminases described herein are stable in organic solvents systems. As used herein stable immobilized transaminases mean that the immobilized transaminase retains its structural conformation or its activity, in organic solvent systems. In one embodiment described herein, the immobilized transaminase is stable in a solvent system that comprises at least 95% of organic solvents.

In certain embodiments described herein, the recombinant transaminase is a transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels measurable by HPLC-UV absorbance.

In yet another embodiment the recombinant transaminase is selected from the group consisting of SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168. Preferably the recombinant transaminase is selected from the group consisting of: SEQ ID NO: 80, 86, 96, 98, 100, 102, 110, or 166. In one embodiment the recombinant transaminase is SEQ ID NO: 102. In another embodiment, the recombinant transaminase is SEQ ID NO: 110.

In certain embodiments of the immobilized transaminases described herein, the resin comprises polymethacrylate with epoxide functional groups, polymethacrylate with amino epoxide functional groups, styrene/DVB copolymer or polymethacrylate with octadecyl functional groups. For example in one embodiment, the resin comprises styrene/DVB copolymer or polymethacrylate with octadecyl functional groups. In another example, the resin is polymethacrylate with epoxide functional groups or polymethacrylate with amino epoxide functional groups. In other embodiments, the resin is selected from the group consisting of SEPABEADS EC-EP, SEPABEADS EC-HFA/S, SEPABEADS EXA252, SEPABEADS EXE119 and SEPABEADS EXE120. For example in one embodiment, the resin is selected from the group consisting of: SEPABEADS EC-EP, SEPABEADS EC-HFA/S and SEPABEADS EXE119. Preferably the resin is selected from the group consisting of: SEPABEADS EXA252 and SEPABEADS EXE120

In one embodiment, of the immobilized transaminase, transaminase SEQ ID NO: 110 physically attached to the resin SEPABEADS EXE120 (Mitsubishi). In another embodiment, the transaminase SEQ ID NO: 102 physically attached to the resin SEPABEADS EXE120 (Mitsubishi).

Also, described herein are methods of making and using the immobilized transaminases. The immobilized transaminases described herein can be used in batch reactions, wherein the immobilized transaminases can be filtered out after the reaction is complete and reused in other reactions. Alternatively, the immobilized transaminases described herein can be used in a continuous reaction system wherein the starting material is continuously passed over the immobilized transaminase and the product is collected.

In one embodiment the process described herein is a process for making (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprising the steps of:

1) dissolving 4-oxo-4-[3-(trifluoromethyl)-5,6-dihydro[1,2,4]triazolo[4,3-c]pyrazin-7(8H)-yl]-1-(2,4,5-trifluorophenyl)butan-2-one in an organic solvent;
2) contacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an immobilized transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in presence of an amino group.

Preferably in such a process the immobilized transaminase is the transaminase SEQ ID NO: 110 physically attached to the resin SEPABEADS EXE120 (Mitsubishi).

Also described herein is a process of making an immobilized transaminase comprising:

1) incubating a solution of transaminase with a resin and an enzyme solution to form an immobilized transaminase;
2) filtering and rinsing the immobilized transaminase;
3) drying the immobilized transaminase.

DETAILED DESCRIPTION OF THE INVENTION

Definitions

"Transaminase", also called "aminotransferase", is used herein to refer to a polypeptide having an enzymatic capability of transferring an amino group ($NH_2$) and a hydrogen atom from a primary amine (3) to an acceptor carbonyl compound (2), converting the amine donor into its corresponding carbonyl compound (4) and the acceptor into its corresponding primary amine (1):

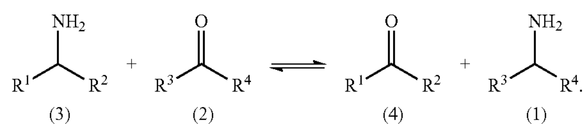

With regard to the immobilized transaminases described herein, the transaminase polypeptides are capable of converting the substrate of formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (the "ketoamide substrate"), to the product of formula (1a) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (the "product) in presence of an amino group donor of formula (3), as follows:

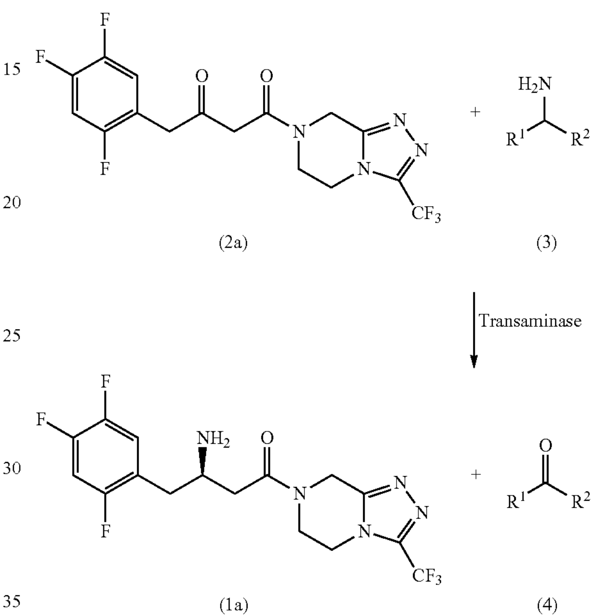

wherein each of $R^1$, $R^2$, $R^3$ and $R^4$ when taken independently, is an alkyl, an alkylaryl group, or aryl group which is unsubstituted or substituted with one or more enzymatically non-inhibiting groups. $R^1$ and $R^3$ can be the same or different from $R^2$ and $R^4$ respectively in structure or chirality. The groups $R^1$ and $R^2$ or $R^3$ and $R^4$, taken together, may form a ring that is unsubstituted, substituted, or fused to other rings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Substrate" as used herein refers to an amino group acceptor, such as a ketone, that accepts the amino group from an amino group donor in a reaction mediated by a transaminase. Substrates can include the compound of formula (II), the compound of formula (2) and the compound of formula (2a), as further described herein. In certain processes described herein, "ketoamide substrate" specifically refers to the compound of formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one.

"Amino group donor" refers to an amino compound which is capable of donating an amino group to an acceptor carbonyl compound (i.e., an amino group acceptor), thereby becoming a carbonyl by-product. Amino group donors are molecules of general formula (3), (3)

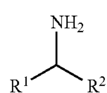

in which each of $R^1$, $R^2$, when taken independently, is an alkyl, an alkylaryl group, or aryl group which is unsubstituted or substituted with one or more enzymatically non-inhibiting groups. $R^1$ can be the same or different from $R^2$ in structure or chirality. The groups $R^1$ and $R^2$, taken together, may form a ring that is unsubstituted, substituted, or fused to other rings. Typical amino group donors that can be used with the invention include chiral and achiral amino acids, and chiral and achiral amines.

"Chiral amine" refers to amines of general formula $R_1$—$CH(NH_2)$—$R_2$ wherein $R_1$ and $R_2$ are nonidentical and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R_1$ and $R_2$ above) also can vary widely and include alkyl, aralkyl, aryl, halo, hydroxy, lower alkyl, lower alkoxy, lower alkylthio, cycloalkyl, carboxy, carboalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Carbonyl by-product" refers to the carbonyl compound formed from the amino group donor when the amino group on the amino group donor is transferred to the amino group acceptor in a transamination reaction. The carbonyl by-product has the general structure of formula (4):

(4)

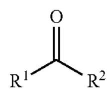

wherein $R_1$ and $R_2$ are defined above for the amino group donor.

"Pyridoxal-phosphate", "PLP", "pyridoxal-5'-phosphate", "PYP", and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7]. Pyridoxal-5'-phosphate is produced in vivo by phosphorylation and oxidation of pyridoxol (also known as pyridoxine or Vitamin B6). In transamination reactions using transaminase enzymes, the amino group of the amino group donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino group acceptor). The transfer of the amino group from pyridoxamine phosphate to the amino acceptor produces a chiral amine and regenerates the coenzyme. The pyridoxal-5'-phosphate of the current invention can be replaced by other members of the vitamin B6 family, including, among others, pyridoxal (PL), pyridoxamine (PM), and their phosphorylated counterparts; pyridoxine phosphate (PNP), and pyridoxamine phosphate (PMP).

"Naturally occurring" or "wild-type" refers to a form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Substantial identity" refers to a polynucleotide or polypeptide sequence that has at least 80 percent sequence identity, preferably at least 85 percent sequence identity, more preferably at least 89 percent sequence identity, more preferably at least 95 percent sequence identity, and even more preferably at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate (e.g., formula (2a)) to its corresponding product (e.g., formula (1a)) with at least about 85% stereoisomeric excess.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a transaminase polypeptide can be expressed as "percent conversion" of the substrate to the product.

"Stable" refers to the ability of the immobilized enzymes described herein to retain their structural conformation and/or their activity in a solvent system that contains organic solvents. In certain embodiments, stable immobilized enzymes lose less than 10% activity per hour in a solvent system that contains organic solvents. Preferably, the stable immobilized enzymes described herein less than 9% activity per hour in a solvent system that contains organic solvents. Preferably, the stable immobilized enzymes described herein less than 8% activity per hour in a solvent system that contains organic solvents. Preferably, the stable immobilized enzymes described herein less than 7% activity per hour in a solvent system that contains organic solvents. Preferably, the stable immobilized enzymes described herein less than 6% activity per hour in a solvent system that contains organic solvents. Preferably, the stable immobilized enzymes described herein less than 5% activity per hour in a solvent system that contains organic solvents. Preferably, the stable immobilized enzymes described herein less than 4% activity per hour in a solvent system that contains organic solvents. Preferably, the stable immobilized enzymes described herein less than 3% activity per hour in a solvent system that contains organic solvents. Preferably, the stable immobilized enzymes described herein less than 2% activity per hour in a solvent system that contains organic solvents. Preferably, the stable immobilized enzymes described herein less than 1% activity per hour in a solvent system that contains organic solvents.

"Amino acid" or "residue" as used in context of the polypeptides disclosed herein refers to the specific monomer at a sequence position (e.g., P8 indicates that the "amino acid" or "residue" at position 8 of SEQ ID NO: 2 is a proline.)

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L Ser (S), L His (H), L Glu (E), L Asn (N), L Gln (Q), L Asp (D), L Lys (K) and L Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L Glu (E) and L Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L Arg (R) and L Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L Asn (N), L Gln (Q), L Ser (S) and L Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L Pro (P), L Ile (I), L Phe (F), L Val (V), L Leu (L), L Trp (W), L Met (M), L Ala (A) and L Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L Phe (F), L Tyr (Y), L His (H) and L Trp (W). L His (H) histidine is classified herein as a hydrophilic residue or as a constrained residue.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L Gly (G), L Leu (L), L Val (V), L Ile (I), L Met (M) and L Ala (A).

"Aliphatic amino acid or residue" refers to a hydrophobic amino acid or residue having an aliphatic hydrocarbon side chain. Genetically encoded aliphatic amino acids include L Ala (A), L Val (V), L Leu (L) and L Ile (I).

"Cysteine" or L Cys (C) is unusual in that it can form disulfide bridges with other L Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L Cys (C) (and other amino acids with SH containing side chains) to exist in a peptide in either the reduced free SH or oxidized disulfide-bridged form affects whether L Cys (C) contributes net hydrophobic or hydrophilic character to a peptide. While L Cys (C) exhibits a hydrophobicity of 0.29 according to the normalized consensus scale of Eisenberg (Eisenberg et al., 1984, supra), it is to be understood that for purposes of the present disclosure L Cys (C) is categorized into its own unique group.

"Hydroxyl-containing amino acid or residue" refers to an amino acid containing a hydroxyl (—OH) moiety. Genetically-encoded hydroxyl-containing amino acids include L Ser (S) L Thr (T) and L-Tyr (Y).

Transaminases

In general, transaminases catalyze the direct amination of ketones to chiral amines. Examples of transaminases include any polypeptide having an enzymatic capability of transferring an amino group ($NH_2$) and a hydrogen atom from a primary amine (3) to an acceptor carbonyl compound (2), converting the amine donor into its corresponding carbonyl compound (4) and the acceptor into its corresponding primary amine (1):

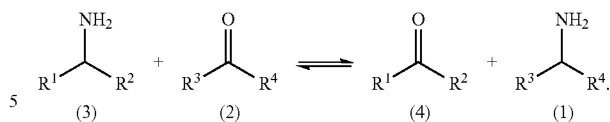

wherein each of $R^1$, $R^2$, $R^3$ and $R^4$ when taken independently, is an alkyl, an alkylaryl group, or aryl group which is unsubstituted or substituted with one or more enzymatically non-inhibiting groups. $R^1$ and $R^3$ can be the same or different from $R^2$ and $R^4$ respectively in structure or chirality. The groups $R^1$ and $R^2$ or $R^3$ and $R^4$, taken together, may form a ring that is unsubstituted, substituted, or fused to other rings.

Described herein are immobilized transaminases comprising recombinant transaminases that are capable of converting 4-oxo-4-[3-(trifluoromethyl)-5,6-dihydro[1,2,4]triazolo [4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product").

In certain embodiments of the immobilized transaminases described herein, the immobilized transaminases include transaminases that are capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product") in the presence of an amino group donor to levels measurable by an analysis technique, such as HPLC-UV absorbance.

In other embodiments of the immobilized transaminases described herein, the immobilized transaminases include transaminases of SEQ ID NO:2. SEQ ID NO: 1 describes the polynucleotide encoding the transaminase polypeptide of SEQ ID NO: 2.

In still yet other embodiments of the immobilized transaminases described herein, the immobilized transaminases include transaminases that are capable of improving conversion of 4-oxo-4-[3-(trifluoromethyl)-5,6-dihydro[1,2,4]triazolo[4,3-a]pyrazin-7(8H)-yl]-1-(2,4,5-trifluorophenyl) butan-2-one ("the ketoamide substrate") to (2R)-4-oxo-4-[3-(trifluoromethyl)-5,6-dihydro[1,2,4]triazolo[4,3-a] pyrazin-7(8H)-yl]-1-(2,4,5-trifluorophenyl)butan-2-amine ("the product"), as compared to SEQ ID NO. 2, in the presence of an amino group donor to levels measurable by an analysis technique, such as HPLC-UV absorbance. Such transaminases are described in U.S. patent application Ser. No. 12/714,397, filed Feb. 26, 2010, which is incorporated herein in its entirety by reference.

In some embodiments, transaminases capable of converting the ketoamide substrate, 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels of product detectable by an analysis technique, such as HPLC-UV absorbance comprise an amino acid sequence corresponding to the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In some embodiments, the transaminases comprise an amino acid sequence that is at least about 80%, 85%, 86%, 87%, 88%, 89%, 90%, 91%, 92%, 93%, 94%, 95%, 96%, 97%, 98%, or 99% identical to a reference sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167 describe the polynucleotides encoding the transaminase polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In certain embodiments of the immobilized transaminases described herein, the transaminase is selected from the group consisting of: SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166 or 168.

In other embodiments of the immobilized transaminases described herein, the transaminase is selected from the group consisting of: SEQ ID NO: 80, 86, 96, 98, 100, 102, 110 or 166.

The immobilized transaminases described herein include a transaminase that is physically attached to a solid support by hydrophobic interactions or chemically attached to a solid support by covalent bonds.

In certain embodiments of the immobilized transaminases described herein, the immobilized transaminases include a transaminase that is physically attached to a solid support by hydrophobic interactions. Suitable transaminases include hydrophobic amino acids or residues i.e. amino acids or residues that include at least one side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L Pro (P), L Ile (I), L Phe (F), L Val (V), L Leu (L), L Trp (W), L Met (M), L Ala (A) and L Tyr (Y). In certain embodiments, the transaminases can include non-polar amino acids or residues such as, but not limited to L Gly (G), L Leu (L), L Val (V), L Ile (I), L Met (M) and L Ala (A). In other embodiments, the transaminases can include aliphatic amino acids or residues such as, but not limited to L Ala (A), L Val (V), L Leu (L) and L Ile (I). In still other embodiments, the transaminases can include aromatic amino acids or residues such as, but not limited to, L Phe (F), L Tyr (Y) and L Trp (W).

A suitable example of a transaminase that is physically attached to a solid support, such as a resin, by hydrophobic interactions is SEQ ID NO: 102. A suitable example of a transaminase that is physically attached to a solid support, such as a resin, by hydrophobic interactions is SEQ ID NO: 110.

In certain embodiments of the immobilized described herein, include a transaminase that is chemically attached to a solid support by covalent bonds. Suitable transaminases include acidic or basic amino acids or residues. Acidic amino acids include L Glu (E) and L Asp (D). Basic amino acids include L Arg (R) and L Lys (K). Other transaminases that can be chemically attached to a solid support include transaminases that include hydrophilic amino acids or residues, hydroxyl-containing amino acids or residues or polar amino acids or residues or transaminases. Still other transaminases that can be chemically attached to a solid support include transaminases that include cysteine. In one example, the transaminase contains L Lys (K) which covalently bonds to a resin containing epoxide functionalities.

A suitable example of a transaminase that is chemically attached to a solid support, such as a resin, by covalent bonds is SEQ ID NO: 102. A suitable example of a transaminase that is chemically attached to a solid support, such as a resin, by covalent bonds is SEQ ID NO: 110.

As described herein, the transaminase polypeptides of the disclosure can be in the form of fusion polypeptides in which the transaminase polypeptides are fused to other polypeptides, such as, by way of example and not limitation, antibody tags (e.g., myc epitope), purifications sequences (e.g., His tags for binding to metals), and cell localization signals (e.g., secretion signals). Thus, the transaminase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α aminoisobutyric acid (Aib); ε aminohexanoic acid (Aha); δ aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4 chlorophenylalanine (Pcf); 2 fluorophenylalanine (Off); 3 fluorophenylalanine (Mff); 4 fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Off); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N acetyl lysine (AcLys); 2,4 diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L or D configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N methyl amino acids (L configuration); 1 aminocyclopent-(2 or 3)-ene-4-carboxylic acid; pipecolic acid; azetidine-3-carboxylic acid; homoproline (hPro); and 1 aminocyclopentane-3-carboxylic acid.

As described above the various modifications introduced into the naturally occurring polypeptide to generate an engineered transaminase enzyme can be targeted to a specific property of the enzyme.

In another aspect, the present disclosure provides polynucleotides encoding the improved transaminase polypeptides. The polynucleotides may be operatively linked to one or more heterologous regulatory sequences that control gene expression to create a recombinant polynucleotide capable of expressing the transaminase polypeptide. Expression constructs containing a heterologous polynucleotide encoding the engineered transaminase can be introduced into appropriate host cells to express the corresponding transaminase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved transaminase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the transaminases (e.g., because the natural sequence can have preferred codons and because use of preferred codons may not be required for all amino acid residues), codon optimized polynucleotides encoding the transaminase polypeptides may contain preferred codons at about 40%, 50%, 60%, 70%, 80%, or greater than 90% of codon positions of the full length coding region.

Solid Support

Described herein are immobilized transaminases comprising a transaminase that is physically or chemically attached to a solid support. Support materials can comprise a wide range of material, either biological, nonbiological, organic, inorganic, or a combination of any of these. For example, the support material may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof. Support materials can be planar crystalline support materials such as silica based support materials (e.g. glass, quartz, or the like), or crystalline support materials used in, e.g., the semiconductor and microprocessor industries, such as silicon, gallium arsenide and the like. Silica aerogels can also be used as support materials, and can be prepared by methods known in the art. Aerogel support materials may be used as free standing substrates or as a surface coating for another support material.

A support material can take any form or shape and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the support material takes an inanimate form, for some attachment peptide applications such as flow cytometry or in situ hybridization, it can be any form that is rigid or semi-rigid. The support material may contain raised or depressed regions on which a capture probe is located. The surface of the support material can be etched using well known techniques to provide for desired surface features, for example trenches, v-grooves, mesa structures, or the like.

Surfaces on the support material can be composed of the same material as the interior part of the support or can be made from a different material, and can be coupled to the interior support material by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed support materials. In one embodiment, the surface is optically transparent and can have surface Si—OH functionalities, such as those found on silica surfaces.

Glass or plastic microscope slides have commonly been used as solid matrix supports for microarray analysis. Opaque matrix-coating materials used to produce microarrays include nylon, PVDF (polyvinylidene fluoride) and nitrocellulose. Nitrocellulose, a traditional polymer substrate in use for more than 50 years, can be used for microarray attachment applications. (E.g., Tonkinson and Stillman, Frontiers in Bioscience 7:c1-12, 2002.) Opaque nitrocellulose has been extensively used to immobilize proteins and nucleic acids for biomolecular analysis. Nitrocellulose immobilizes molecules of interest in near quantitative fashion and allows for short and long term storage. Nitrocellulose also allows for solution phase target species to efficiently bind to immobilized entities.

A solid support may be of any suitable composition to which the attachment molecule may be applied. It may be pretreated or functionalized prior to application of the attachment/molecule peptide to facilitate binding of the attachment molecules, or for any other desired purpose, such as fostering conditions favorable for the activity or any other desired property of the entity or avoiding undesired interactions with other entities. Many such surface treatments and/or functionalizations are known in the art and selection of a suitable treatment and/or functionalization will depend upon the identity and characteristics of the attachment molecule/peptide and entity and upon the attendant conditions and desired activity.

With regard to the immobilized transaminases described herein the solid support is a resin. Resins can be made from any suitable composition including, but not limited to, polymethacrylate and styrene/DVB copolymer. Such resins can include functional groups and facilitate the convalent bonding of the recombinant transaminase to the resin. Suitable functional groups include, but are not limited to, epoxide and amino epoxide. Additionally, other functional groups such as octadecyl and resins that include a porous structure facilitate in generating hydrophobic interactions with the recombinant transaminase.

In certain embodiments of the immobilized transaminases described herein, the resin comprises polymethacrylate with epoxide functional groups, polymethacrylate with amino epoxide functional groups, styrene/DVB copolymer or polymethacrylate with octadecyl functional groups. Examples of suitable resins include, but are not limited to, SEPABEADS EC-EP, SEPABEADS EC-HFA/S, SEPABEADS EXA252, SEPABEADS EXE119 and SEPABEADS EXE120.

The following table includes suitable resins that can be used in connection with the immobilized transaminases described herein:

TABLE 1

| Resin Name (Mitsubishi) | Resin Composition | Resin Functional Group |
|---|---|---|
| SEPABEADS EC-EP | polymethacrylate | epoxide |
| SEPABEADS EC-HFA/S | polymethacrylate | amino epoxide |
| SEPABEADS EXA252 | styrene/DVB copolymer | porous structure |
| SEPABEADS EXE119 | polymethacrylate | epoxide |
| SEPABEADS EXE120 | polymethacrylate | octadecyl |

In certain embodiments of the immobilized described herein, the immobilized transaminase includes a resin that is physically attached to the transaminase by hydrophobic interactions. Suitable resins comprise styrene/DVB copolymer or polymethacrylate with octadecyl functional groups. Examples include, but are not limited to, SEPABEADS EXA252 and SEPABEADS EXE120.

In other embodiments of the immobilizeds described herein, the immobilized transaminase includes a resin that is chemically attached to a transaminase by covalent bonds. Suitable resins comprise polymethacrylate with epoxide functional groups or polymethacrylate with amino epoxide functional groups. Examples include, but are not limited to, SEPABEADS EC-EP, SEPABEADS EC-HFA/S and SEPABEADS EXE119.

In still other embodiments of the immobilized described herein, the immobilized transaminase is comprised of the transaminase SEQ ID NO: 102 physically attached to the resin SEPABEADS EXE120 (Mitsubishi). In still other embodiments of the immobilized described herein, the immobilized transaminase is comprised of the transaminase SEQ ID NO: 110 physically attached to the resin SEPABEADS EXE120 (Mitsubishi).

Process for Making the Immobilized Transaminase

Also described herein are processes for making the immobilized transaminase. In certain embodiments of the processes for making the immobilized transaminases described herein, the process begins with making a buffered solution of the transaminase. The transaminase polypeptide may use pyridoxal phosphate (PLP) as a coenzyme, which may be bound to the enzyme when prepared, e.g., as provided by the host cell in which the polypeptide is expressed. In some embodiments, PLP, PLP analogs, or precursors to PLP can be added to the media of host cells during expression of the transaminase polypeptide. In some embodiments of the processes, PLP or PLP analogs can be added to a reaction to provide the coenzyme required for enzyme activity. The amount of PLP sufficient for enzyme activity can be determined by one of skill in the art.

In some embodiments of the processes for making the immobilized transaminase, the transaminase solution can comprise a pH of about 5.0 to about 9.0. In some embodiments, the reaction condition for the process is a pH of about 7.5.

The process further comprises contacting or incubating the transaminase with a resin, by adding the resin to the solution. The solution is then agitated for a length of time, such as overnight.

In some embodiments, the reaction condition for carrying out the process can comprise a temperature of about 5° C. to about 70° C. In some embodiments, the reaction condition is a temperature of about 25° C. (room temperature).

Once the reaction if complete the immobilized transaminase is filtered and rinsed. After the immobilized enzyme is rinsed with buffer, in certain embodiments of the processes described herein, the preparation is dried before it is used in a 100% organic solvent system. The immobilized enzyme can be dried under vacuum with a nitrogen sweep to remove water from the outer surface of the immobilized enzyme resin. The immobilized preparation can be stirred while drying to allow for even moisture content throughout the immobilized enzyme bed and to prevent over- or under-drying any portion of the immobilized enzyme preparation. The immobilized preparation can also be dried by washing with organic solvents. Over-drying can result in loss of activity as water is stripped away from the enzyme molecule attached to the resin. Under-drying can result in insufficient mass transfer in an organic solvent system to affect the transamination of the desired substrate.

Processes for Using the Immobilized Transaminase

The immobilized transaminases described herein can be used to transfer an amino group ($NH_2$) and a hydrogen atom from a primary amine to an acceptor carbonyl compound, converting the amine donor into its corresponding carbonyl compound and the acceptor into its corresponding primary amine. Such a process comprises contacting the acceptor carbonyl compound with an immobilized transaminase described herein in presence of an amino group donor in a suitable organic solvent under suitable reaction conditions wherein the acceptor carbonyl compound is converted to its corresponding primary amine.

In some embodiments, the immobilized transaminases can be used in a process for preparing a compound of structural formula (I):

(I)

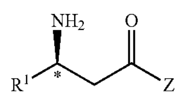

having the indicated stereochemical configuration at the stereogenic center marked with an *; in an enantiomeric excess of at least 70% over the opposite enantiomer, wherein Z is $OR^2$ or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, NH, and $NC_{0-4}$ alkyl, the heterocyclic ring being unsubstituted or substituted with one to three substituents independently selected from oxo, hydroxy, halogen, $C_{1-4}$ alkoxy, and $C_{1-4}$ alkyl, wherein alkyl and alkoxy are unsubstituted or substituted with one to five fluorines; and the heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{0-4}$ alkyl, the fused ring system being unsubstituted or substituted with one to two substituents selected from hydroxy, amino, fluorine, $C_{1-4}$ alkyl, $C_{1-4}$ alkoxy, and trifluoromethyl. In these embodiments, the process comprises the step of contacting a prochiral ketone of structural formula (II):

(II)

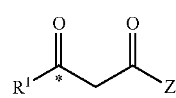

with an immobilized transaminase polypeptide in the presence of an amino group donor in a suitable organic solvent under suitable reaction conditions for the conversion of the compound of formula (II) to the compound of formula (I).

In some embodiments of the process, the $R^1$ of formula (II) is benzyl, wherein the phenyl group of benzyl is unsubstituted or substituted with one to three substituents selected from the group consisting of fluorine, trifluoromethyl, and trifluoromethoxy.

In some embodiments of the process, the Z of formula (II) is $NR^2R^3$.

In some embodiments of the process, the $NR^2R^3$ of formula (II) is a heterocycle of the structural formula (III):

(III)

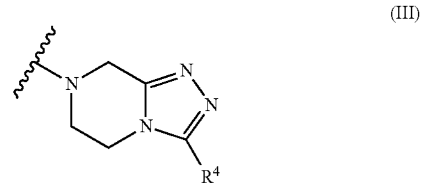

wherein $R^4$ is hydrogen or $C_{1-4}$ alkyl which is unsubstituted or substituted with one to five fluorines.

In some embodiments, the immobilized transaminases can be used in a process for preparing a compound of structural formula (1):

(1)

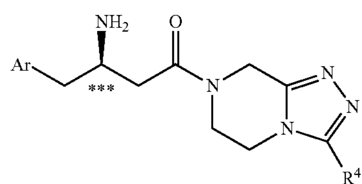

having the (R)-configuration at the stereogenic center marked with an ***, in an enantiomeric excess of at least 70% over the enantiomer having the opposite (S)-configuration; wherein Ar is phenyl which is unsubstituted or substituted with one to five substituents independently selected from the group consisting of fluorine, trifluoromethyl, and trifluoromethoxy; and $R^4$ is hydrogen or $C_{1-4}$ alkyl unsubstituted or substituted with one to five fluorines. In such embodiments, the process comprises the step of contacting a prochiral ketone of structural formula (2):

(2)

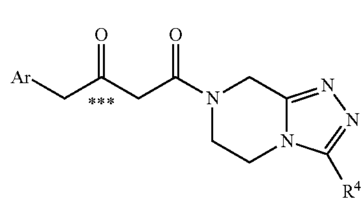

with an immobilized transaminase polypeptide disclosed herein in the presence of an amino group donor in a suitable organic solvent under suitable reaction conditions for the conversion of the compound of formula (2) to the compound of formula (1).

In some embodiments of the process, the Ar of formula (2) is 2,5-difluorophenyl or 2,4,5-trifluorophenyl, and $R^4$ is trifluoromethyl.

In some embodiments of the process, the Ar of formula (2) is 2,4,5-trifluorophenyl.

In some embodiments, the transaminases can be used in a process for preparing a compound of formula (1a), (2R)-4-oxo-4-[3-(trifluoromethyl)-5,6-dihydro[1,2,4]triazolo[4,3-c]pyrazin-7(8H)-yl]-1-(2,4,5-trifluorophenyl)butan-2-amine, in enantiomeric excess:

(1a)

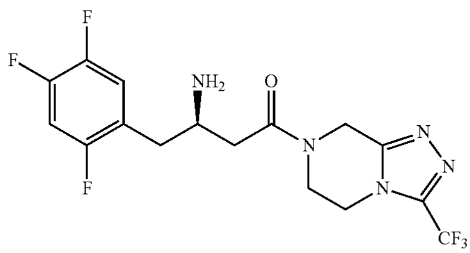

In these embodiments, the process comprises the step of contacting a prochiral ketone of structural formula (2a), 4-oxo-4-[3-(trifluoromethyl)-5,6-dihydro[1,2,4]thiazolo[4,3-a]pyrazin-7(8H)-yl]-1-(2,4,5-trifluorophenyl)butan-2-one):

(2a)

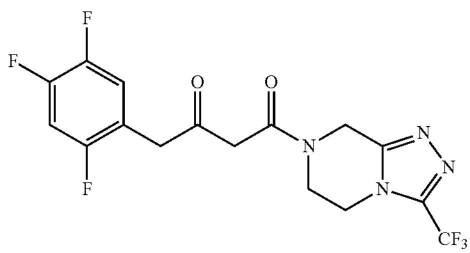

with an immobilized transaminase described herein in the presence of an amino group donor in a suitable organic solvent under suitable reaction conditions for the conversion of the compound of formula (2a) to the compound of formula (1a).

In some embodiments of the processes above, the compound of formula (1), the compound of formula (1) or the compound of formula (1a) is produced in at least 70%, 80%, 90%, 91%, 92%, 93%, 94%, 95%, 96%, 97%, 98%, 99% or more enantiomeric excess.

In some embodiments of the processes, the compound of formula (I), the compound of formula (1) or the compound of formula (1a) is produced in at least 99% enantiomeric excess.

The compound of formula (II), the compound of formula (2), and the compound of formula (2a), along with their syntheses, are described in, among others, U.S. Pat. Nos. 7,326,708 and 7,468,459, the disclosures of which are incorporated herein by reference in their entirety.

In some embodiments, the process of using the immobilized transaminases described herein comprises the steps of: 1) dissolving 4-oxo-4-[3-(trifluoromethyl)-5,6-dihydro[1,2,4]triazolo[4,3-a]pyrazin-7(8H)-yl]-1-(2,4,5-trifluorophenyl)butan-2-one in an organic solvent; 2) contacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an immobilized transaminase described herein in the presence of an amino group.

Described herein are immobilized transaminases comprising a recombinant transaminase attached to a resin by covalent bonds or hydrophobic interactions, wherein the transaminase is stable in organic solvents. Suitable organic solvents that can be used in the processes described herein include any organic solvent commonly known in the art such as, methanol, ethanol, THF, DMSO, toluene, isopropylacetate, hexanes, propanol, benzene, acetone, xylene, methylethyl ketone, ether and ethyl acetate. In certain examples of the processes described herein the organic solvent is isopropylacetate.

In certain embodiments the organic solvent is a non-water saturated solvent. In other embodiments the organic solvent is a water-saturated solvent. Water saturation may keep the immobilized enzyme at a constant water concentration and prevents further drying of the immobilized enzyme over the course of the reaction. This can allow for greater operational stability when the immobilized enzyme is isolated at the end of the reaction and reused for multiple batches. In certain examples of the processes described herein the organic solvent is water-saturated isopropylacetate.

In certain embodiments the solvent that the transaminase is stable in is a component of a solvent system. In certain embodiments of the processes for using the immobilized transaminases described herein, the solvent system is a 100% organic solvent system. In other embodiments the solvent system contains 50-60% organic solvents. Preferably, the solvent system contains 60-70% organic solvents. More preferably, the solvent system contains 70-80% organic solvents. More preferably, the solvent system contains 80-90% organic solvents. More preferably, the solvent system contains 90-100% organic solvents. In other embodiments the solvent system contains at least 50% organic solvents. In other embodiments the solvent system contains at least 55% organic solvents. Preferably, the solvent system contains at least 60% organic solvents. Preferably, the solvent system contains at least 65% organic solvents. More preferably, the solvent system contains at least 70% organic solvents. More preferably, the solvent system contains at least 75% organic solvents. More preferably, the solvent system contains at least 80% organic solvents. More preferably, the solvent system contains at least 85% organic solvents. More preferably, the solvent system contains at least 90% organic solvents. More preferably, the solvent system contains at least 95% organic solvents. More preferably, the solvent system contains at least 100% organic solvents. The solvent system can contain more than one organic solvent, wherein the immobilized transaminase is stable in one or all of the organic solvents present in the solvent system.

As discussed above, the amino group donor used in the process can be a chiral amine or an achiral amine. An achiral amino group donor has the advantage of not being limited in its reaction to a specific stereoisomer, thus requiring less of the amino group donor. Various suitable amino group donors can be used, including, by way of example and not limitation, isopropylamine (also referred to as 2-aminopropane), L, D or DL alanine, phenylalanine, glutamate, glutamine, leucine (or any other suitable α-amino acids), 3-aminobutyric acid (or any other suitable β-amino acids), and methylbenzylamine. In some embodiments, the amino group donor is isopropylamine. In some embodiments, other amino group donors may be used, including, among others, α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-aspartic acid, L-lysine, L-ornithine, β-alanine, taurine, n-octylamine, cyclohexylamine, 1,4-butanediamine, 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines. In certain examples of the processes described herein the amine donor is isopropylamine.

In certain examples of the processes described herein the immobilized transaminase is the transaminase SEQ ID NO: 102 physically attached to the resin SEPABEADS EXE120 (Mitsubishi). In certain examples of the processes described herein the immobilized transaminase is the transaminase SEQ ID NO: 110 physically attached to the resin SEPABEADS EXE120 (Mitsubishi).

In some embodiments of the processes described above, the immobilized transaminases described herein can be recycled, wherein once the immobilized transaminases are filtered off once the reaction is complete and used in subsequent reactions. Thus certain processes described herein can further comprise the step of filtering off the immobilized transaminase and to be used in subsequent reactions.

In some embodiments of the processes above, a step in the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product.

Removal of the carbonyl by-product can be carried in a number of ways. Where the amino group donor is an amino acid, such as alanine, the carbonyl by product, a keto acid, can be removed by reaction with peroxide (see, e.g., US 2008/0213845, incorporated herein by reference). Peroxides which can be used include, among others, hydrogen peroxide; peroxyacids (peracids) such as peracetic acid ($CH_3CO_3H$), trifluoroperacetic acid and metachloroperoxybenzoic acid; organic peroxides such as t-butyl peroxide ($(CH_3)_3COOH$), or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation to carbon dioxide acetaldehyde by employing pyruvate decarboxylase (see, e.g., Höhne et al., 2008, Chem BioChem 9: 363-365).

In some embodiments, where the choice of the amino group donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas.

In some embodiments, the amino acid donor used in the process is isopropylamine, which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a ketoreductase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal. Alternatively, in embodiments where an amino acid is used as amino group donor, the keto acid carbonyl by-product can be recycled back to the amino acid by reaction with ammonia and NADH using an appropriate amino acid dehydrogenase enzyme, thereby replenishing the amino group donor.

The processes of using the immobilized transaminases described herein include batch process and continuous process. Continuous processes include processes wherein the ketone substrate is continuously contacting the immobilized transaminase and wherein the product is continuously being collected. Examples include wherein the immobilized transaminase is packed in a column and a solution of the ketone substrate is passed through the column. Thus the ketone is continuously contacting the immobilized resin and the product is collected after is has passed through the column.

In some embodiments, the process for converting ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprises dissolving the ketoamide substrate 4-oxo-4-[3-(trifluoromethyl)-5,6-dihydro[1,2,4]triazolo[4,3-c]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in isopropylacetate; contacting the ketoamide substrate with an immobilized transaminase described herein under reaction conditions of a temperature of 30 to 50° C. in presence of isopropylamine of from about 1 M to about 2 M, wherein at least 80%, 85%, 90%, 92%, 94%, 96%, or 98% or more of the ketoamide substrate is converted to product in 24 hrs. In some embodiments, the immobilized transaminase capable of carrying out the foregoing reaction comprises an amino acid sequence corresponding to SEQ ID NO: 80, 86, 96, 98, 100, 102, 110, or 166 physically or chemically attached to a resin comprising SEPABEADS EXE119, SEPABEADS EXE120, SEPABEADS EC-EP, SEPABEADS EC-HFA/S and SEPABEADS EXA252.

In some embodiments, the processes above can further comprise the step of isolating the compound of structural formula (I), the compound of structural formula (1), or the compound of structural formula (1a) from the reaction solvent.

In some embodiments, the processes above can further comprise a step of converting the compound of structural formula (1) or the compound of structural formula (1a) into a pharmaceutically acceptable salt by contacting the compound with a pharmaceutically acceptable acid in a suitable reaction solvent. In some embodiments, the pharmaceutically acceptable acid is phosphoric acid and the pharmaceutically acceptable salt is the dihydrogenphosphate salt. In some embodiments, the salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine is the phosphate monohydrate salt, having the following chemical formula:

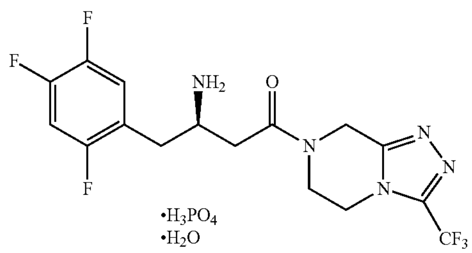 [SMILES: N[C@@H](CC(=O)N1CCn2c(nnc2C(F)(F)F)C1)Cc1cc(F)c(F)cc1F]

In some embodiments, in a process for the preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate (1:1) monohydrate, the improvement in the process comprises a step of converting the compound of formula (1a) to the compound of formula (2a) with an immobilized transaminase described herein in presence of an amino group donor in a suitable organic solvent under suitable reaction conditions, wherein the compound of formula (1a) is (1a)

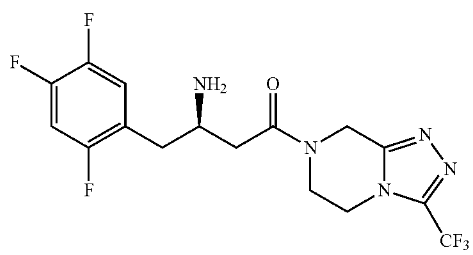

and the compound of formula (2a) is:

(2a)

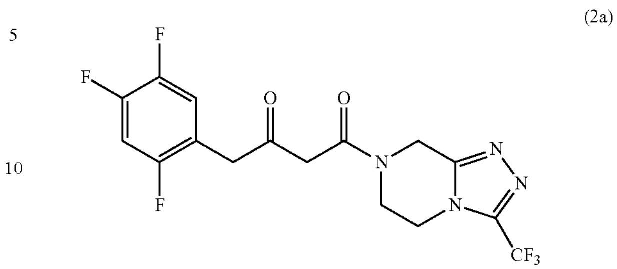

In some embodiments of the preparation of the phosphate monohydrate salt, the amino donor is isopropylamine.

Methods for preparing various salts are described in U.S. Pat. Nos. 7,326,708 and 7,468,459, each of which is hereby incorporated by reference herein.

EXAMPLES

Examples 1-5

Immobilization of Transaminase

Five different resins, as shown in Table 2, were evaluated.

TABLE 2

| Example | Resin | Composition |
|---|---|---|
| 1 | SEPABEADS EC-EP | polymethacrylate/epoxide |
| 2 | SEPABEADS EC-HFA/S | polymethacrylate/amino epoxide |
| 3 | SEPABEADS EXA252 | styrene/DVB copolymer |
| 4 | SEPABEADS EXE119 | polymethacrylate/epoxide |
| 5 | SEPABEADS EXE120 | polymethacrylate/octadecyl |

A 25 g/L solution of SEQ ID NO: 110 in 100 mM potassium phosphate buffer (pH 7.5) with 1 g/L PLP (pyrodoxial-5-phosphate) was made. 1 g of each resin was incubated with 5 mL of enzyme solution in a shaker overnight at room temperature. The resin was filtered away from the transaminase solution and rinsed 5 times with 5 mL 100 mM potassium phosphate buffer (pH 7.5). Resin performance was then evaluated vs. the lyophilized enzyme preparation in the following transamination:

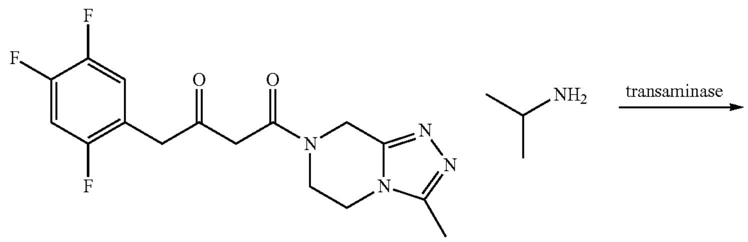

-continued

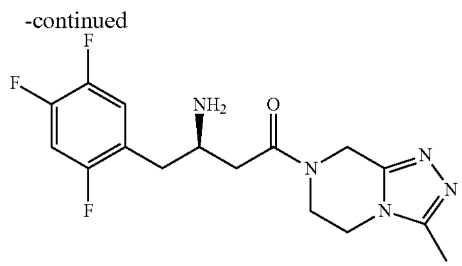

The immobilized transaminase preparations exhibited good specific activity compared to the lyophilized enzyme.

Example 6

Evaluation of the SEPABEADS EXE120 Resin Drying Procedure and Demonstration of Immobilized Enzyme Activity in the 100% Organic Solvent System The immobilized enzyme (SEQ ID NO: 110/SEPABEADS EXE120 resin) was dried under vacuum with a nitrogen sweep to remove water from the outer surface of the immobilized enzyme resin. The immobilized preparation was stirred while drying to allow for even moisture content throughout the immobilized enzyme bed and to prevent over- or under-drying any portion of the immobilized enzyme preparation. 100 mg of ketoamide substrate was dissolved in 1 mL water saturated IPAc (isopropylacetate). 40 uL IPM (isopropyl amine) was added to the reaction solution. 100 mg of dried immobilized transaminase (SEQ ID NO: 110/SEPABEADS EXE120 resin) was added to the reaction. The reaction was stirred in a Thermomixer at 1000 rpm and 50° C. Samples were taken over 70 hours and conversion and ee were determined. >99.9% ee of the desired amine product was obtained. The immobilized transaminase exhibited reasonable activity as compared to the lyophilized free enzyme which exhibited no activity in the IPAc reaction system.

Example 7

Plug Flow Reaction (PFR) Process for the Manufacture of Sitagliptin in IPAc 10 mL of ketonamide substrate solution was made (100 g/L-400 g/L ketone, 40 uL/mL-160 uL/mL isopropylamine in IPAc). 0.75 g of immobilized transaminase (SEQ ID NO: 110/SEPABEADS EXE120 resin) was slurry packed in a column under gravity using IPAc. The substrate solution was fed via syringe pump to the column, which was jacketed at 50° C. The flow rate was set to 0.1 mL/h.

At steady state, 85-90% conversion to the sitagliptin amine (>99% ee) was observed at the outlet of the column.

What is claimed is:

1. An immobilized transaminase comprising:

a recombinant transaminase that is SEQ ID NO: 110; and a resin, wherein the recombinant transaminase is attached to the resin, wherein the resin comprises polymethacrylate with epoxide functional groups, polymethacrylate with amino epoxide functional groups, styrene/DVB copolymer or polymethacrylate with octadecyl functional groups and wherein the immobilized transaminase loses less than 10% activity per hour in a solvent system that comprises at least 90% of organic solvents.

2. An immobilized transaminase of claim 1 wherein the immobilized transaminase loses less than 10% activity per hour in a solvent system that comprises at least 95% of organic solvents.

3. A process for making (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprising the steps of:

1) dissolving 4-oxo-4-[3-(trifluoromethyl)-5,6-dihydro[1,2,4]triazolo[4,3-a]pyrazin-7(8H)-yl]-1-(2,4,5-trifluorophenyl)butan-2-one in an organic solvent;

2) contacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an immobilized transaminase of claim 1 in presence of an amino group.

4. A process of making an immobilized transaminase comprising:

1) incubating a solution of transaminase with a resin and an enzyme solution to form an immobilized transaminase, wherein that transaminase is SEQ ID NO: 110 and the resin comprises polymethacrylate with epoxide functional groups, polymethacrylate with amino epoxide functional groups, styrene/DVB copolymer or polymethacrylate with octadecyl functional groups;

2) filtering and rinsing the immobilized transaminase; and 3) drying the immobilized transaminase, wherein the immobilized transaminase loses less than 10% activity per hour in a solvent system that comprises at least 90% of organic solvents.

* * * * *